(12) United States Patent
Constantino

(10) Patent No.: US 9,782,466 B2
(45) Date of Patent: *Oct. 10, 2017

(54) CAPSULAR POLYSACCHARIDE SOLUBILISATION AND COMBINATION VACCINES

(75) Inventor: Paolo Constantino, Siena (IT)

(73) Assignee: GLAXOSMITHKLINE BIOLOGICALS SA (BE)

(*) Notice: Subject to any disclaimer, the term of this patent is extended or adjusted under 35 U.S.C. 154(b) by 0 days.

This patent is subject to a terminal disclaimer.

(21) Appl. No.: 12/321,418

(22) Filed: Jan. 20, 2009

(65) Prior Publication Data
US 2009/0181049 A1 Jul. 16, 2009

Related U.S. Application Data

(62) Division of application No. 10/481,457, filed as application No. PCT/IB02/03191 on Jun. 20, 2002, now Pat. No. 8,753,651.

(30) Foreign Application Priority Data

Jun. 20, 2001 (GB) .................................. 0115176.0

(51) Int. Cl.
| | | |
|---|---|---|
| *A61K 39/385* | (2006.01) | |
| *A61K 45/00* | (2006.01) | |
| *A61K 47/00* | (2006.01) | |
| *A61K 39/00* | (2006.01) | |
| *A61K 39/095* | (2006.01) | |
| *A61K 39/102* | (2006.01) | |
| *A61K 39/09* | (2006.01) | |
| *A61K 39/08* | (2006.01) | |
| *C09F 1/02* | (2006.01) | |
| *A23J 1/00* | (2006.01) | |
| *C07K 1/00* | (2006.01) | |
| *C07K 14/00* | (2006.01) | |
| *C07K 16/00* | (2006.01) | |
| *C07K 17/00* | (2006.01) | |
| *C07K 1/06* | (2006.01) | |
| *C07K 1/08* | (2006.01) | |
| *C09F 1/00* | (2006.01) | |
| *A23J 1/04* | (2006.01) | |
| *A61K 38/00* | (2006.01) | |
| *A23J 1/20* | (2006.01) | |
| *C07H 15/04* | (2006.01) | |
| *C07K 14/22* | (2006.01) | |
| *C07K 14/285* | (2006.01) | |
| *A61K 38/48* | (2006.01) | |

(52) U.S. Cl.
CPC ............ *A61K 39/095* (2013.01); *A23J 1/04* (2013.01); *A23J 1/205* (2013.01); *A61K 38/00* (2013.01); *A61K 38/4893* (2013.01); *A61K 39/092* (2013.01); *A61K 39/102* (2013.01); *A61K 2039/545* (2013.01); *A61K 2039/55505* (2013.01); *A61K 2039/6037* (2013.01); *C07H 15/04* (2013.01); *C07K 14/22* (2013.01); *C07K 14/285* (2013.01); *C09F 1/00* (2013.01); *Y10S 424/831* (2013.01)

(58) Field of Classification Search
CPC .... A61K 39/095; A61K 38/00; A61K 39/092; A61K 38/4893; A61K 39/102; A61K 39/39; A61K 2039/545; A61K 2039/55505; A61K 2039/6037; C09F 1/00; C07H 15/04; C07K 14/22; Y10S 424/831
See application file for complete search history.

(56) References Cited

U.S. PATENT DOCUMENTS

| | | |
|---|---|---|
| 4,123,520 A | 10/1978 | Hagopian et al. |
| 4,206,200 A | 6/1980 | Guthorhlein et al. |
| 4,220,717 A | 9/1980 | Kuo |
| 4,242,501 A | 12/1980 | Cano et al. |
| 4,351,762 A | 9/1982 | Verlander et al. |
| 4,451,446 A | 5/1984 | Vandevelde et al. |
| 4,496,538 A | 1/1985 | Gordon |
| 4,740,589 A * | 4/1988 | Moreno .................. 424/197.11 |
| 4,753,796 A | 6/1988 | Moreno et al. |
| 4,761,283 A | 8/1988 | Anderson |

(Continued)

FOREIGN PATENT DOCUMENTS

| | | |
|---|---|---|
| EP | 0 245 045 | 5/1987 |
| EP | 0 072 513 | 3/1989 |

(Continued)

OTHER PUBLICATIONS

Costantino et al. (Vaccine, 1992; 10: 691-698).*
Frasch, Bacterial Vaccines, 1990: 123-145.*
Ambrosch et al. "Immunogenicity and Side-effects of a New Tetravalent Meningococcal Polysaccharide Vaccine," (Bulletin of the World Health Organization, 61(2): 317-323 (1983).
Bartoloni et al. "Immunogenicity of meningococcal B polysaccharide conjugated to tetanus toxoid or CRM197 via adipic acid dihydrazide," Vaccine, 13(5): 463-470 (1995).
Peltola. "Meningococcal vaccines. Current status and future possibilities," Drugs, 55(3): 347-366 (1998).
Goebel. "Chemo-Immunological Studies on Conjugated Carbohydrate-Proteins," The Journal of Experimental Medicine, 68: 469-484 (1938).

(Continued)

*Primary Examiner* — Gary Nickol
*Assistant Examiner* — Lakia Jackson-Tongue
(74) *Attorney, Agent, or Firm* — Lisa Matovcik

(57) ABSTRACT

Precipitated bacterial capsular polysaccharides can be efficiently re-solubilized using alcohols as solvents. The invention provides a process for purifying a bacterial capsular polysaccharide, comprising the steps of (a) precipitation of said polysaccharide, followed by (b) solubilization of the precipitated polysaccharide using ethanol. CTAB can be used for step (a). The material obtained, preferably following hydrolysis and sizing, can be conjugated to a carrier protein and formulated as a vaccine. Also, in vaccines comprising saccharides from both serogroups A and C, the invention provides that the ratio (w/w) of MenA saccharide: MenC saccharide is >1.

14 Claims, 21 Drawing Sheets

(56) References Cited

U.S. PATENT DOCUMENTS

| | | | |
|---|---|---|---|
| 4,762,713 | A | 8/1988 | Anderson |
| 4,814,276 | A | 3/1989 | Evans et al. |
| 4,963,534 | A | 10/1990 | Calabria |
| 5,314,811 | A | 5/1994 | Lee et al. |
| 5,490,937 | A * | 2/1996 | van Reis ............ 210/637 |
| 5,693,326 | A * | 12/1997 | Lees ............ 424/194.1 |
| 5,811,102 | A | 9/1998 | Jennings et al. |
| 5,847,112 | A | 12/1998 | Kniskern et al. |
| 5,965,714 | A | 10/1999 | Ryall |
| 6,007,818 | A | 12/1999 | Moreau |
| 6,013,264 | A | 1/2000 | Petre et al. |
| 6,045,805 | A | 4/2000 | Moreau |
| 6,087,328 | A | 7/2000 | Lees |
| 6,146,902 | A | 11/2000 | McMaster |
| 6,248,334 | B1 | 6/2001 | Lees et al. |
| 6,248,570 | B1 | 6/2001 | Michon et al. |
| 6,413,520 | B1 | 7/2002 | Granoff |
| 6,472,506 | B1 | 10/2002 | Moreau et al. |
| 6,531,131 | B1 | 3/2003 | Gu et al. |
| 6,632,437 | B1 | 10/2003 | Schneerson et al. |
| 6,696,065 | B1 * | 2/2004 | Fahim et al. ............ 424/254.1 |
| 2002/0054879 | A1 | 5/2002 | Lees et al. |
| 2002/0054884 | A1 | 5/2002 | Peetermans et al. |
| 2002/0182226 | A1 | 12/2002 | Peetermans et al. |
| 2003/0068336 | A1 * | 4/2003 | Ryall ............ 424/250.1 |
| 2003/0157129 | A1 | 8/2003 | Slaoui et al. |
| 2005/0106181 | A1 | 5/2005 | Constantino |
| 2005/0208605 | A1 | 9/2005 | Stanton et al. |
| 2007/0082014 | A1 | 4/2007 | Costantino |
| 2009/0098156 | A1 | 4/2009 | Danzig |
| 2009/0130140 | A1 * | 5/2009 | Costantino ............ 424/197.11 |
| 2009/0130147 | A1 * | 5/2009 | Constantino ............ 424/236.1 |
| 2009/0181053 | A1 * | 7/2009 | Constantino ............ 424/236.1 |
| 2009/0182128 | A1 * | 7/2009 | Costantino ............ 530/402 |
| 2009/0182129 | A1 * | 7/2009 | Costantino ............ 530/411 |
| 2009/0297553 | A1 | 12/2009 | Danzig |
| 2010/0291138 | A1 * | 11/2010 | Capiau et al. ............ 424/197.11 |

FOREIGN PATENT DOCUMENTS

| | | |
|---|---|---|
| EP | 0 398 615 | 11/1990 |
| EP | 0 528 635 | 2/1993 |
| EP | 833662 | 4/1998 |
| EP | 630260 | 1/2001 |
| EP | 562107 | 5/2002 |
| WO | WO 87/06838 | 11/1987 |
| WO | 89/00860 | 2/1989 |
| WO | WO 90/06696 | 6/1990 |
| WO | WO 92/16232 | 10/1992 |
| WO | WO 93/07178 | 4/1993 |
| WO | 95/08348 A1 | 3/1995 |
| WO | WO 96/14086 | 5/1996 |
| WO | WO 96/40242 | 12/1996 |
| WO | 97/28273 | 8/1997 |
| WO | WO 97/30171 | 8/1997 |
| WO | WO 98/08543 A | 3/1998 |
| WO | 98/31393 A2 | 7/1998 |
| WO | WO 98/30239 | 7/1998 |
| WO | WO 98/32873 A | 7/1998 |
| WO | WO 98/45312 | 10/1998 |
| WO | WO 98/47530 | 10/1998 |
| WO | WO 98/54296 | 12/1998 |
| WO | WO 98/58670 | 12/1998 |
| WO | WO 99/18121 | 4/1999 |
| WO | WO 99/32653 | 7/1999 |
| WO | WO 99/42130 | 8/1999 |
| WO | WO 99/61053 | 12/1999 |
| WO | WO 00/38711 | 7/2000 |
| WO | WO 00/56358 | 9/2000 |
| WO | WO 00/56359 | 9/2000 |
| WO | WO 00/56360 | 9/2000 |
| WO | WO 00/71725 | 11/2000 |
| WO | WO 01/09350 | 2/2001 |
| WO | WO 01/30390 | 5/2001 |
| WO | WO 01/41800 | 6/2001 |
| WO | 01/64920 A | 9/2001 |
| WO | 01/64922 A | 9/2001 |
| WO | WO 02/00249 | 1/2002 |
| WO | 02/22167 A | 3/2002 |
| WO | WO 02/058737 A | 8/2002 |
| WO | 03/007985 A | 1/2003 |
| WO | 03/020756 A | 3/2003 |
| WO | 03/028661 A | 4/2003 |
| WO | 03/080678 A | 10/2003 |
| WO | 03/094834 A | 11/2003 |
| WO | 03/094960 A | 11/2003 |
| WO | 2004/019992 A | 3/2004 |
| WO | 2004/032958 A | 4/2004 |

OTHER PUBLICATIONS

Gotschlich et al. "Human Immunity to Meningococcus," The Journal of Experimental Medicine, 129: 1385-1395 (1969).

Bundle et al. "Determination of the Structure and Conformation of Bacterial Polysaccharides by Carbon 13 . . . " The Journal of Biological Chemistry, 249(7): 2275-2281 (1974).

Jennings et al. "Structures of the Capsular Polysaccharides of *Neisseria meningitidis* as Determined by [13]C . . . " The Journal of Infectious Diseases, 136 Supp: S78-S83 (1977).

Robbins. "Vaccines for the Prevention of Encapsulated Bacterial Diseases: Current Status, Problems and Prospects for the Future," Immunochemistry, 15: 839-854 (1978).

Costantino et al. "Development and Phase 1 Clinical Testing of a Conjugate Vaccine Against Meningococcus A and C," Vaccine, 10: 691-698 (1992).

Avendano et al. "*Haemophilus influenzae* type b polysaccharide-tetanus protein conjugate vaccine does not depress . . . " Pediatric Infectious Disease Journal,12(8): 638-643 (1993).

Giebink et al. "Pneumococcal Capsular Polysaccharide-Meningococcal Outer Membrane Protein Complex Conjugate . . . " The Journal of Infectious Diseases, 167: 347-355 (1993).

Twumasi et al. "A Trial of a Group A plus Group C Meningococcal Polysaccharides-Protein Complex Conjugate Vaccine . . . " The Journal of Infectious Diseases, 171: 632-638 (1995).

Paoletti et al. "Neonatal Mouse Protection against Infection with Multiple Group B Streptococcal (GBS) Serotypes by Maternal . . . " Infection and Immunity,62(8): 3236-3243 (1994).

Andre et al. "Conventional and New Generation Combined Vaccines," Modern Vaccinology: 41-54 (1994).

Lindberg. "Glycoprotein conjugate vaccines," Vaccine, 17: S28-S36 (1999).

Campagne et al. "Safety and immunogenicity of three doses of a *Neisseria meningitidis* A+C diptheria conjugate . . . " Pediatric Infectious Disease Journal, 19(2): 144-150 (2000).

Lieberman et al. "Safety and immunogenicity of a serogroups A/C *Neisseria meningitidis* oligosaccharide-protein conjugate vaccine in young . . . " JAMA, 275(19): 1499-1503 (1996).

Levine, et al. "Cost Effectiveness Analysis for Routine . . . " Conj Polysaccharide Vaccines, Poster 74, Abstracts 10th International Path. *Neisseria* Conf. pp. 228-230 (1997).

American Society of Tropical Medicine and Hygiene, 46th Annual Meeting, Dec. 7-11, 1997, Disney's Coronado Springs Resort, Lake Buena Vista, Florida: pp. 129-130.

Anderson et al. "Safety and Immunogenicity of Meningococcal A and C Polysaccharide Conjugate Vaccine in Adults," Infection and Immunity: 3391-3395 (1994).

Lamb et al. "Capillary Electrophoretic Analysis of Meningococcal Polysaccharide—Diptheria Toxoid Conjugate Vaccines," Dev. Biol. Basel, Karger, 103: 251-258 (2000).

Lei et al. "Quantification of Free Polysaccharide in Meningococcal Polysaccharide-Diptheria Toxoid Conjugate Vaccines," Dev. Biol. Basel, Karger, 103: 259-264 (2000).

Lindberg. "Polyosides (encapsulated bacteria)," Life Sciences, 322: 925-932 (1999).

Perkins. "New Opportunities for Prevention of Meningococcal Disease," JAMA, 282 (21): 2842-2843 (2000).

Vaccines (3rd Ed.) eds. Plotkin & Orenstein p. 722-723 (1999).

(56) References Cited

OTHER PUBLICATIONS

"Structure of Neisserial Proteins," 10th International Pathogenic *Neisseria* Conference (1996).
"Conjugate and Polysaccharide Vaccines," 10th International Pathogenic *Neisseria* Conference (1996).
Fusco et al. "Meningococcal Vaccine Development: A Novel Approach," Exp Opin Invest Drugs, 7: 245-252 (1998).
"Prevention and Control of Meningococcal Disease: Recommendations of the Advisory Committee on Immunization Practices (ACIP)," MMWR 49(RR-07): 1-10 (Jun. 30, 2000).
Minutes of the Advisory Committee on Immunization Practices (ACIP) Meeting (Oct. 2000).
ACIP Charter, www.cdc.gov/nip/acip/chapter.htm, May 9, 2006.
Global Alliance for Vaccines and Immunization (GAVI), Fourth Board Meeting, Noordwijk, The Netherlands (Nov. 19, 2000).
Fusco et al. "Preclinical Studies on a Group Y Meningococcal Conjugate Vaccine," Abstract 251, 39th Interscience Conference on Antimicrobial Agents and Chemotherapy, CA (1999).
Notice of Opposition, dated Jan. 5, 2007, filed in counterpart European Patent EP 1 401 489 B1.
Kennedy et al. "The Isolation of Xanthan Gum from Fermentations of Xanthomonas Campestris by Complexation with Quaternary Ammonium . . . " Carbohydrate Proteins, 1: 55-66 (1981).
Scott. "Fractionation by Precipitation with Quartemary Ammonium Salts," Methods in Carbohydrate Chemistry, 8: 38-44 (1965).
Chapter 12 (*Haemophilus influenzae* Vaccines) of Vaccines, Plotkin & Mortimer, Second Edition (1994).
Chapter 17 (Meningococcal Vaccines) of Vaccines, Plotkin & Mortimer, Second Edition (1994).
Beuvery et al. "Immunological evaluation of meningococcal group C polysaccharide-tetanus toxoid conjugate in mice," Infect Immun. 41 (2): 609-17 (1983).
Campbell et al. "Safety, reactogenicity, and immunogenicity of a tetravalent meningococcal polysaccharide-diphtheria toxoid . . . " J Infect Dis., 186(120): 1848-51 (2002).
Granoff. "Meningococcal polysaccharide-protein conjugate vaccines," Abstracts of the 10th International Pathogenic *Neisseria* Conference, Baltimore USA: 203-208 (1996).
Lingappa et al. "Active Bacterial Core surveillance (ABCs) team. Surveillance for meningococcal disease and strategies for use of conjugate . . . " Vaccine, 19(31): 4566-75 (2001).
Lindberg et al. "Structural studies on the specific type-14 pneumococcal polysaccharide," Carbohydr Res, 58 (1): 177-86 (1977).
Lee. "Bacterial capsular polysaccharides-biochemistry, immunity and vaccine," Mol Immunol, 24 (10): 1005-19 (1987).
Morley et al. "Vaccine prevention of meningococcal disease, coming soon?" Vaccine, 20 (5-6): 666-87 (2001).
Rappuoli. "Conjugate and reverse vaccinology to eliminate bacterial meningitis." Vaccine, 19 (17-19): 2319-22 (2001).
Rennels et al. "Dose escalation, safety and immunogenicity study of a tetravalent meningococcal polysaccharide diphtheria . . . " Pediatr Infect Dis J., 21 (10): 987-9 (2002).
Opposition's Submission Before Oral Proceeding in European Patent Application No. 02755452.6; Aug. 25, 2008.
Declaration of Dr. Anne Vandercammen submitted with Opponent's Submission Before Oral Proceeding in European Patent Application No. 02755452.6; Aug. 25, 2008.
Paradiso et al. "Glyconconjugate vaccines: future combinations," Dev Biol Stand, 87: 269-75 (1996).
Robbins et al. "Prevention of invasive bacterial diseases by immunization with polysaccharide-protein conjugates," Curr Top Microbiol Immunol, 146: 169-80 (1989).
Scott. "Aliphatic ammonium salts in the assay of acidic polysaccharides from tissues," Methods Biochem Anal, 8: 145-97 (1960).
Smidsrod et al. "Precipitation of acidic polysaccharides by salts in ethanol-water mixtures," J Polymer Science, 16: 1587-1598 (1967).
Tai et al. "Preclinical evaluation of a combination vaccine against groups A . . . " Abstracts of the 10th International Pathogenic *Neisseria* Conference, Baltimore: 214-5 (1996).
Chu, C. et al., "Further Studies on the Immunogenicity of Haemophilus Influenzae Type b and Pneumococcal Type 6A Polysaccharide-Protein Conjugates," Infection and Immunity, 40(1):245-256 (1983).
Frasch, C., "Production and Control of Neisseria meningitidis Vaccines," Advances in Biological Processes, 13:123-145 (1990).
Klein, D., "Pneumococcal Conjugate Vaccines: Review and Update," Microbial Drug Resistance, 1(1): 49-58 (1995).
"WHO Expert Committee on Biological Standardization," WHO Technical Report Series, No. 594, pp. 66-67 (1976).
Novartis Media Release, "New Data for Menveo(TM) Vaccine Show Excellent Immune Response and Broad Protection for Infants Against Meningococcal Meningitidis," Nov. 15, 2007.
Rodrigues, L. et al., "Immunity to Hemophilus Influenzae Type b," J. Immunol., 107(4): 1071-1080 (1971).
Tanizaki, M. et al., "Purification of Meningococcal Group C Polysaccharide by a Procedure Suitable for Scale-Up," J. Microb. Meth., 27:19-23 (1969).
Patentee's Reply to Notice of Opposition in European Patent Application No. 02755452.6; Aug. 24, 2007.
Summons to Attend Oral Proceedings in European Patent Application No. 02755452.6; May 30, 2008.
Opponent's Submission Before Oral Proceedings in European Patent Application No. 02755452.6; Aug. 22, 2008.
Minutes of Oral Proceedings in European Patent Application No. 02755452.6; Jan. 8, 2009.
Interlocutory Decision in Opposition Proceedings in European Patent Application No. 02755452.6; Jan. 8, 2009.
Opponent's Notice of Appeal from Opposition Division's Decision in European Patent Application No. 02755452.6; Dec. 22, 2008.
Opponent's Statement of Grounds of Appeal Against Decision of Opposition Division in European Application No. 02755452.6; Apr. 17, 2009.
Opponent's Submissions in response to Patentee's Grounds of Appeal in European Application No. 02755452.6; Sep. 22, 2009.
Patentee's Submission in response to Opponent's Grounds of Appeal in European Application No. 02755452.6; Oct. 13, 2009.
Annex to Summons to Attend Oral Proceedings in Appeal Proceeding in European Application No. 02755452.6; Oct. 20, 2009.
Patentee's Submission Before Oral Proceedings in European Patent Application No. 02755452.6; Nov. 13, 2009.
Opponent's Submission Before Oral Proceedings in European Patent Application No. 02755452.6; Nov. 25, 2009.
Decision of the Technical Board of Appeal in European Patent Application No. 02755452.6; Dec. 23, 2009.
Extracts from the transcript of a hearing on Oct. 2, 2009 in UK Proceedings.
Table of conjugate vaccines available before priority date.
Vaccines (2nd Ed.) Eds. Plotkin and Mortimer, chapter 28 (Meningococcal Vaccines), pp. 711-727 (1994).
Lee, et al., "Capsular polysaccharide of clostridium perfringens," Infection Immunity, 10: 318-322 (1974).
Lepow, M. et al., "Meningococcal Vaccines," Vaccines, Third Edition, Chapter 28, W.B. Sauders Company, pp. 711-727.
P. Costantino et al., "Size Fractionation of Bacterial Capsular Polysaccharides For Their Use In Conjugate Vaccines", Vaccine 17:1251-1263 (1999).
A. Leach et al., "Induction of Immunologic Memory in Gambian Children by Vaccination in Infancy with a Group A plus Group C Meningococcal Polysaccharide-Protein Conjugate Vaccine", J. Infect. Dis. 175:200-204 (1997).
J. Amir et al., "Immunogenicity and Safety Of A Liquid Combination of DT-PRP-T vs Lyophilizied PRP-T Reconstituted With DTP", Vaccine 15(2): 149-154 (1997).
D.M. Granoff et al., "MF59 Adjuvant Enhances Antibody Responses of Infant Baboons Immunized with Haemophilus influenzae Type b and Neisseria meningitidis Group C Oligosaccharide-CRM197 Conjugate Vaccine", Infect. Immunity 65(5): 1710-1715 (1997).
N. Ravenscroft et al., "Size Determination of Bacterial Capsular Oligosaccharides Used to Prepare Conjugate Vaccines", Vaccine 17: 2802-2816 (1999).

(56) References Cited

OTHER PUBLICATIONS

M.J. Corbel, "Reasons for Instability of Bacterial Vaccines", Dev. Biol. Stand. 87: 113-124 (1996).

C.-Y. Lee et al., "An Evaluation of the Safety and Immunogenicity of a Five-Compound Acellular Pertussis, Dipththeria, and Tetanus Toxoid Vaccine (DTaP) When Combined With a Haemophilus influenzae Type b-Tetantus Toxoid Conjugate Vaccine (PRP-T) in Taiwanese Infants", Paediatrics 103(1): 25-30 (1999).

L.C. Paoletti, "Potency of Clinical Group B Streptococcal Conjugate Vaccines", Vaccine 19(15-16): 2118-2126 (2001).

E.C. Gotschlich et al., "Human Immunity to the Meningococcus. III. Preparation and Immunochemical Properties the Group A, Group B, and Group C Meningococcal Polysaccharides, " J. Exp. Med. 129(6): 1349-1365 (1969).

E.C. Beuvery et al., "Preparation and Immunochemical Characterization Of Meningococcal Group C Polysaccharide-Tetanus Toxoid Conjugates As A New Generation Of Vaccines." Infect. Immun. 40(1): 39-45 (1983).

* cited by examiner

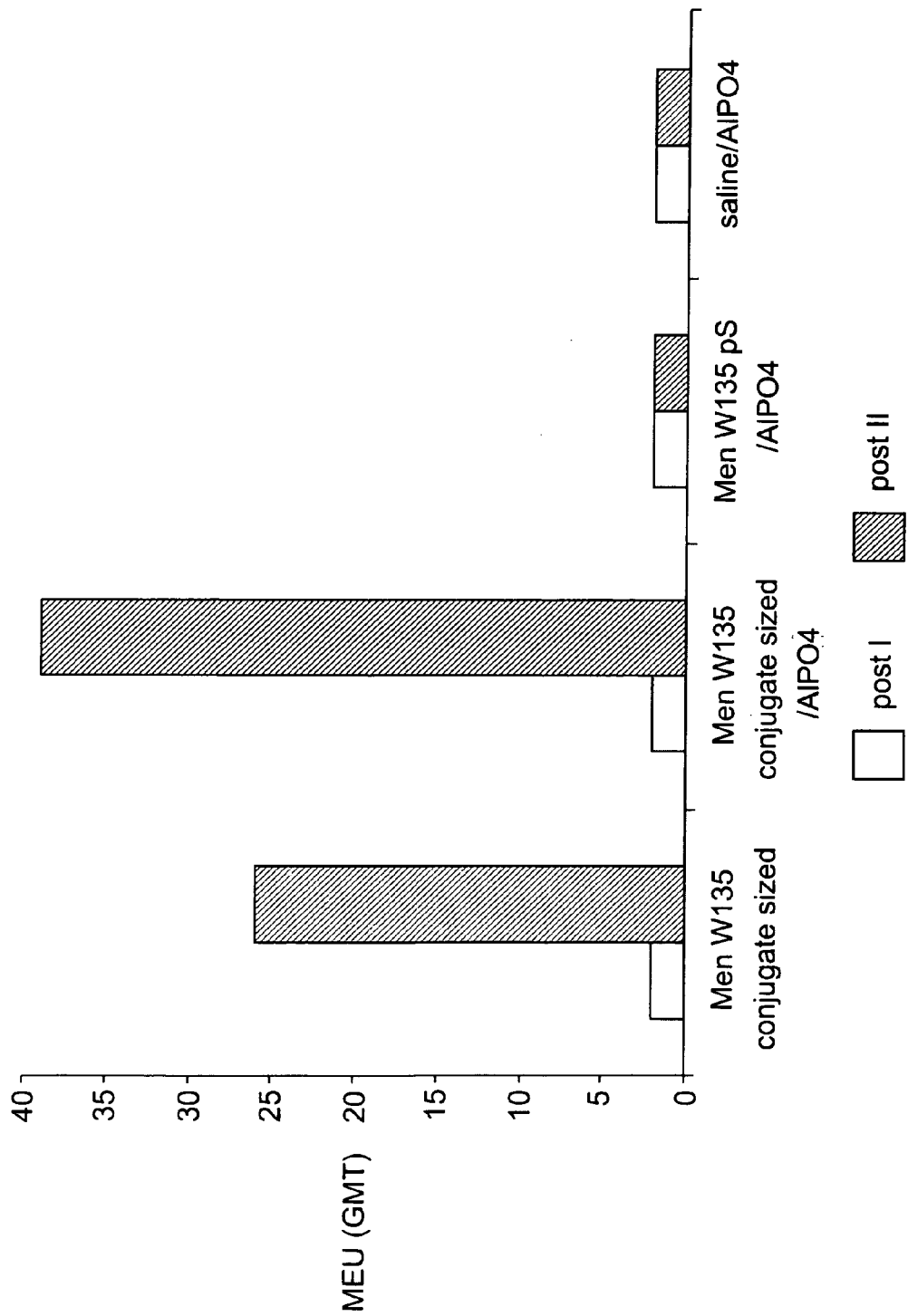

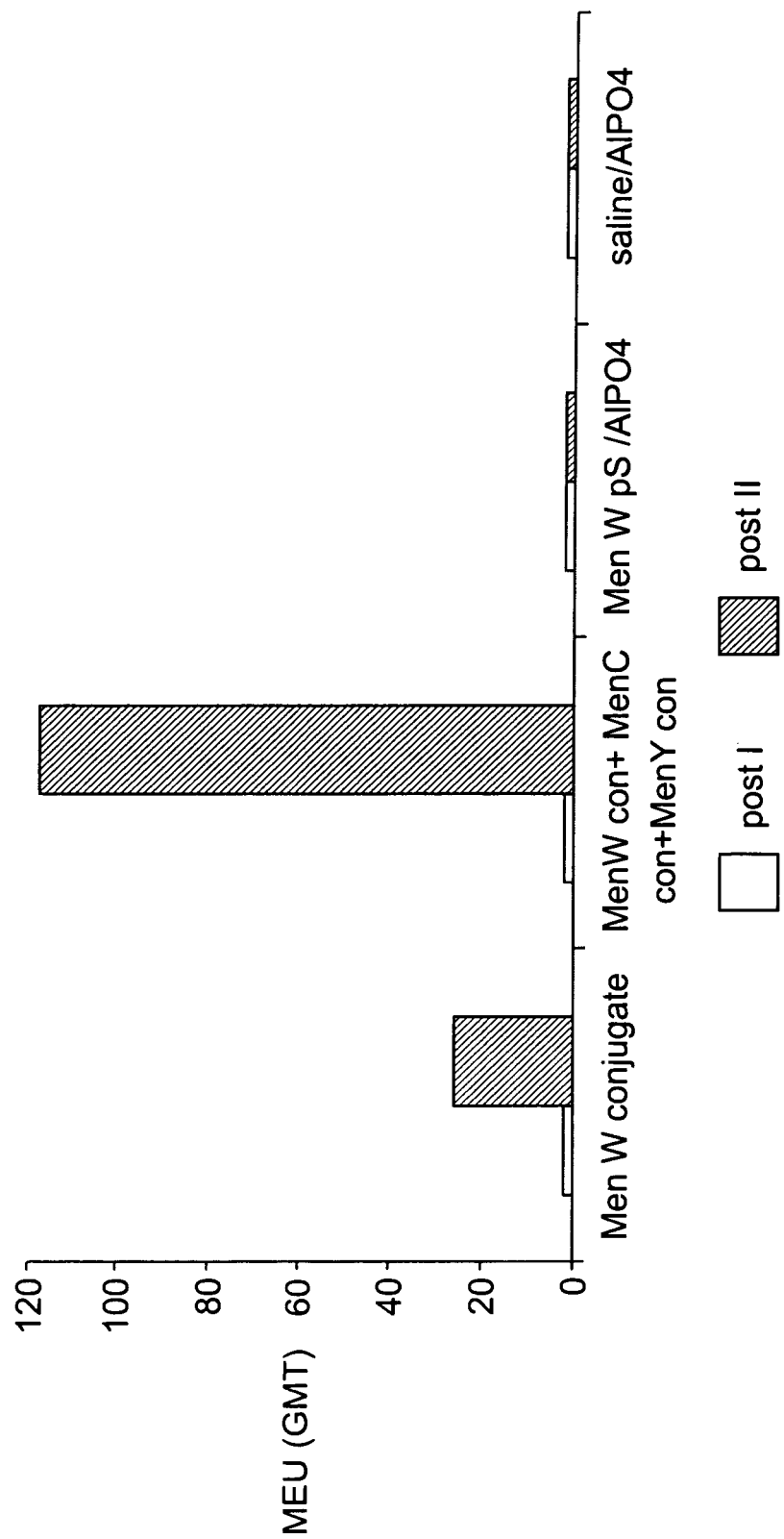

CAPSULAR POLYSACCHARIDE SOLUBILISATION AND COMBINATION VACCINES

CROSS REFERENCE TO RELATED APPLICATIONS

This application is a Divisional Application of U.S. application Ser. No. 10/481,457 filed Dec. 3, 2004, which is the U.S. National Phase of International Application No. PCT/IB02/03191, filed Jun. 20, 2002 and published in English, which claims priority to G.B. Application No. 0115176.0, filed Jun. 20, 2001. The teachings of the above applications are incorporated in their entirety by reference.

TECHNICAL FIELD

This invention is in the field of vaccines, particularly against meningococcal infection and disease.

BACKGROUND ART

*Neisseria meningitidis* is a Gram negative human pathogen. It colonises the pharynx, causing meningitis and, occasionally, septicaemia in the absence of meningitis. It is closely related to *N. gonorrhoeae*, although one feature that clearly differentiates meningococcus is the presence of a polysaccharide capsule that is present in all pathogenic meningococci.

Based on the organism's capsular polysaccharide, twelve serogroups of *N. meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries.

Capsular polysaccharides from *N. meningitidis* are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 1].

A tetravalent vaccine of capsular polysaccharides from serogroups A, C, Y and W135 has been known for many years [2, 3] and has been licensed for human use. Although effective in adolescents and adults, it induces a poor immune response and short duration of protection and cannot be used in infants [e.g. 4]. This is because polysaccharides are T cell-independent antigens that induce a weak immune response that cannot be boosted. The polysaccharides in this vaccine are not conjugated and are present at a 1:1:1:1 ratio [5]. MENCEVAX ACWY™ contains 50 µg of each purified polysaccharide once reconstituted from its lyophilised form.

Conjugated serogroup C oligosaccharides have also been approved for human use [e.g. MENJUGATE™; ref. 6]. There remains, however, a need for improvements in conjugate vaccines against serogroups A, W135 and Y, and in their manufacture.

DISCLOSURE OF THE INVENTION

The invention provides a process for purifying a bacterial capsular polysaccharide, comprising the steps of (a) precipitation of said polysaccharide, followed by (b) solubilisation of the precipitated polysaccharide using ethanol. The polysaccharide can be used to prepare vaccines, such as conjugate vaccines, in particular against *N. meningitidis* serogroups A, W 135 and Y.

Precipitation and Ethanol Solubilisation

Many techniques for precipitating soluble polysaccharides are known in the art. Preferred methods use one or more cationic detergents. The detergents preferably have the following general formula:

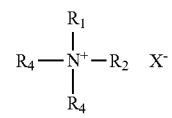

wherein: $R_1$, $R_2$ and $R_3$ are the same or different and each signifies alkyl or aryl; or $R_1$ and $R_2$ together with the nitrogen atom to which these are attached form a 5- or 6-membered saturated heterocyclic ring, and $R_3$ signifies alkyl or aryl; or $R_1$, $R_2$ and $R_3$ together with the nitrogen atom to which these are attached form a 5- or 6-membered heterocyclic ring, unsaturated at the nitrogen atom, $R_4$ signifies alkyl or aryl, and $X^-$ signifies an anion.

Particularly preferred detergents for use in the method are tetrabutylammonium and cetyltrimethylammonium salts (e.g. the bromide salts). Cetyltrimethylammonium bromide ('CTAB') is particularly preferred [8]. CTAB is also known as hexadecyltrimethylammonium bromide, cetrimonium bromide, Cetavlon and Centimide. Other detergents include hexadimethrine bromide and myristyltrimethylammonium salts.

Capsular polysaccharides are released into media during culture. Accordingly, the starting material for precipitation will typically be the supernatant from a centrifuged bacterial culture or will be a concentrated culture.

The precipitation step may be selective for polysaccharides, but it will typically also co-precipitate other components (e.g. proteins, nucleic acid etc.).

Precipitated polysaccharide may be collected by centrifugation prior to solubilisation.

After precipitation, the polysaccharide (typically in the form of a complex with the cationic detergent) is re-solubilised. It is preferred to use a solvent which is relatively selective for the polysaccharide in order to minimise contaminants (e.g. proteins, nucleic acid etc.). Ethanol has been found to be advantageous in this respect, and it is highly selective for the CTAB-polysaccharide complex. Other lower alcohols may be used (e.g. methanol, propan-1-ol, propan-2-ol, butan-1-ol, butan-2-ol, 2-methyl-propan-1-ol, 2-methyl-propan-2-ol, diols etc.)

The ethanol is preferably added to the precipitated polysaccharide to give a final ethanol concentration (based on total content of ethanol and water) of between 50% and 95% (e.g. around 55%, 60%, 65%, 70%, 75%, 80%, 85%, or around 90%), and preferably between 75% and 95%. The optimum final ethanol concentration may depend on the serogroup of the bacterium from which the polysaccharide is obtained.

The ethanol may be added to the precipitated polysaccharide in pure form or may be added in a form diluted with a miscible solvent (e.g. water). Preferred solvent mixtures are ethanol:water mixtures, with a preferred ratio of between around 70:30 and around 95:5 (e.g. 75:25, 80:20, 85:15, 90:10).

Compared with conventional processes for preparing capsular polysaccharides, the two-step process of precipitation followed by ethanol extraction is quicker and simpler.

In contrast to the process described in ref. 9, the process uses cationic detergent rather than anionic detergent. Unlike the process of ref. 10, the polysaccharide is re-solubilised using ethanol, rather than by cation exchange using calcium or magnesium salts. Unlike the process of ref. 11, precipitation does not require an inert porous support. Furthermore, unlike prior art processes, alcohol is used to re-solubilise the polysaccharide rather than to precipitate it.

The bacterial capsular polysaccharide will usually be from *Neisseria*. Preferably it is from *N. meningitidis*, including serogroups A, B, C, W135 & Y. Preferred serogroups are A, W135 & Y. The process is also suitable for preparing capsular polysaccharide from *Haemophilus influenzae* (particularly type B, or 'Hib') and from *Streptococcus pneumoniae* (pneumococcus).

Further Processing of the Solubilised Polysaccharide

After re-solubilisation, the polysaccharide may be further treated to remove contaminants. This is particularly important in situations where even minor contamination is not acceptable (e.g. for human vaccine production). This will typically involve one or more steps of filtration.

Depth filtration may be used. This is particularly useful for clarification.

Filtration through activated carbon may be used. This is useful for removing pigments and trace organic compounds. It can be repeated until, for example, $OD_{275nm} < 0.2$.

Size filtration or ultrafiltration may be used.

Once filtered to remove contaminants, the polysaccharide may be precipitated for further treatment and/or processing. This can be conveniently achieved by exchanging cations (e.g. by the addition of calcium or sodium salts).

The polysaccharide may be chemically modified. For instance, it may be modified to replace one or more hydroxyl groups with blocking groups. This is particularly useful for MenA [12]. Polysaccharides from serogroup B may be N-propionylated [13].

The (optionally modified) polysaccharide will typically be hydrolysed to form oligosaccharides. This is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; etc.). Oligosaccharides are preferred to polysaccharides for use in vaccines. DP can conveniently be measured by ion exchange chromatography or by colorimetric assays [14].

If hydrolysis is performed, the hydrolysate will generally be sized in order to remove short-length oligosaccharides. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

To enhance immunogenicity, polysaccharides or oligosaccharides of the invention are preferably conjugated to a carrier (FIG. 18). Conjugation to carrier proteins is particularly useful for paediatric vaccines [e.g. ref. 15] and is a well known technique [e.g. reviewed in refs. 16 to 24, etc.].

Preferred carrier proteins are bacterial toxins or toxoids, such as diphtheria or tetanus toxoids. The $CRM_{197}$ diphtheria toxoid [25, 26, 27] is particularly preferred. Other suitable carrier proteins include the *N. meningitidis* outer membrane protein [28], synthetic peptides [29, 30], heat shock proteins [31, 32], pertussis proteins [33, 34], cytokines [35], lymphokines [35], hormones [35], growth factors [35], artificial proteins comprising multiple human CD4+ T cell epitopes from various pathogen-derived antigens [36], protein D from *H. influenzae* [37], toxin A or B from *C. difficile* [38], etc. It is possible to use mixtures of carrier proteins.

Conjugates with a saccharide:protein ratio (w/w) of between 0.5:1 (i.e. excess protein) and 5:1 (i.e. excess saccharide) are preferred, and those with a ratio between 1:1.25 and 1:2.5 are more preferred.

A single carrier protein may carry multiple different saccharides [39]. Conjugates may be used in conjunction with free carrier protein [40].

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [41, 42, etc.]). Other suitable techniques use carbodiimides, hydrazides, active esters, norborane, p-nitrobenzoic acid, N-hydroxysuccinimide, S-NHS, EDC, TSTU; see also the introduction to reference 22).

Linkages via a linker group may be made using any known procedure, for example, the procedures described in references 43 and 44. One type of linkage involves reductive amination of the polysaccharide, coupling the resulting amino group with one end of an adipic acid linker group, and then coupling a protein to the other end of the adipic acid linker group [20, 45, 46]. Other linkers include B-propionamido [47], nitrophenyl-ethylamine [48], haloacyl halides [49], glycosidic linkages [50], 6-aminocaproic acid [51], ADH [52], $C_4$ to $C_{12}$ moieties [53] etc. As an alternative to using a linker, direct linkage can be used. Direct linkages to the protein may comprise oxidation of the polysaccharide followed by reductive amination with the protein, as described in, for example, references 54 and 55.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred.

After conjugation, free and conjugated saccharides can be separated. There are many suitable methods, including hydrophobic chromatography, tangential ultrafiltration, diafiltration etc. [see also refs. 56 & 57, etc.].

Mixtures and Compositions Comprising the Saccharides

The oligosaccharides, polysaccharides and conjugates of the invention may mixed with other biological molecules. Mixtures of saccharides from more than one serogroup of *N. meningitidis* are preferred e.g. compositions comprising saccharides from serogroups A+C, A+W135, A+Y, C+W135, C+Y, W135+Y, A+C+W135, A+C+Y, C+W135+Y, A+C+W135+Y, etc. It is preferred that the protective efficacy of individual saccharide antigens is not removed by combining them, although actual immunogenicity (e.g. ELISA titres) may be reduced.

Where a saccharide from serogroup C is used, this preferably has from ~12 to ~22 repeating units.

Saccharides from different serogroups of *N. meningitidis* may be conjugated to the same or different carrier proteins.

Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Surprisingly, improved immunogenicity of the MenA component has been observed when it is present in excess (mass/dose) to the MenC component.

Where a mixture comprises capsular saccharides (e.g. oligosaccharides) from serogroup W135 and at least one of serogroups A, C and Y, it has surprisingly been found that the immunogenicity of the MenW135 saccharide is greater when administered in combination with the saccharide(s) from the other serogroup(s) than when administered alone (at the same dosage etc.) [cf. ref. 58]. Thus the capacity of the MenW135 antigen to elicit an immune response is greater than the immune response elicited by an equivalent amount of the same antigen when delivered without association with the antigens from the other serogroups. Such enhanced immunogenicity can be determined by administering the MenW135 antigen to control animals and the mixture to test animals and comparing antibody titres against the two using standard assays such as bactericidal titres, radioimmunoassay and ELISAs etc. Vaccines comprising synergistic combinations of saccharides from serogroup W135 and other serogroups are immunologically advantageous. They allow enhanced anti-W135 responses and/or lower W135 doses.

Where a mixture comprises capsular saccharides from serogroup Y and one or both of serogroups C and W135, it is preferred that the ratio (w/w) of MenY saccharide:MenW135 saccharide is greater than 1 (e.g. 2:1, 3:1, 4:1, 5:1, 10:1 or higher) and/or that the ratio (w/w) of MenY saccharide:MenC saccharide is less than 1 (e.g. 1:2, 1:3, 1:4, 1:5, or lower).

Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1.

The mixtures may also comprise proteins. It is preferred to include proteins from serogroup B of *N. meningitidis* [e.g. refs. 59 to 64] or OMV preparations [e.g. refs. 65 to 68 etc.].

Non-meningococcal and non-neisserial antigens, preferably ones that do not diminish the immune response against the meningococcal components, may also be included. Ref. 69, for instance, discloses combinations of oligosaccharides from *N. meningitidis* serogroups B and C together with the Hib saccharide. Antigens from pneumococcus, hepatitis A virus, hepatitis B virus, *B. pertussis*, diphtheria, tetanus, *Helicobacter pylori*, polio and/or *H. influenzae* are preferred. Particularly preferred non-neisserial antigens include:

- antigens from *Helicobacter pylori* such as CagA [70 to 73], VacA [74, 75], NAP [76, 77, 78], HopX [e.g. 79], HopY [e.g. 79] and/or urease.
- a saccharide antigen from *Streptococcus pneumoniae* [e.g. 80, 81, 82].
- an antigen from hepatitis A virus, such as inactivated virus [e.g. 83, 84].
- an antigen from hepatitis B virus, such as the surface and/or core antigens [e.g. 84, 85], with surface antigen preferably being adsorbed onto an aluminium phosphate [86].
- a saccharide antigen from *Haemophilus influenzae* B [e.g. 87], preferably non-adsorbed or adsorbed onto an aluminium phosphate [88].
- an antigen from hepatitis C virus [e.g. 89].
- an antigen from *N. gonorrhoeae* [e.g. 59 to 62].
- an antigen from *Chlamydia pneumoniae* [e.g. refs. 90 to 96].
- an antigen from *Chlamydia trachomatis* [e.g. 97].
- an antigen from *Porphyromonas gingivalis* [e.g. 98].
- polio antigen(s) [e.g. 99, 100] such as IPV.
- rabies antigen(s) [e.g. 101] such as lyophilised inactivated virus [e.g. 102, RabAvert™].
- measles, mumps and/or rubella antigens [e.g. chapters 9, 10 & 11 of ref. 103].
- influenza antigen(s) [e.g. chapter 19 of ref. 103], such as the haemagglutinin and/or neuraminidase surface proteins.
- an antigen from *Moraxella catarrhalis* [e.g. 104].
- an antigen from *Streptococcus agalactiae* (group B streptococcus) [e.g. 105, 106].
- an antigen from *Streptococcus pyogenes* (group A streptococcus) [e.g. 106, 107, 108].
- an antigen from *Staphylococcus aureus* [e.g. 109].
- antigen(s) from a paramyxovirus such as respiratory syncytial virus (RSV [110, 111]) and/or parainfluenza virus (PIV3 [112]).
- an antigen from *Bacillus anthracis* [e.g. 113, 114, 115].
- an antigen from a virus in the flaviviridae family (genus *flavivirus*), such as from yellow fever virus, Japanese encephalitis virus, four serotypes of Dengue viruses, tick-borne encephalitis virus, West Nile virus.
- a pestivirus antigen, such as from classical porcine fever virus, bovine viral diarrhoea virus, and/or border disease virus.
- a parvovirus antigen e.g from parvovirus B19.
- a tetanus toxoid [e.g. ref. 116].
- pertussis holotoxin (PT) and filamentous haemagglutinin (FHA) from *B. pertussis*, optionally also in combination with pertactin and/or agglutinogens 2 and 3 [e.g. refs. 117 & 118].
- cellular pertussis antigen.

The mixture may comprise one or more of these further antigens, which may be detoxified where necessary (e.g. detoxification of pertussis toxin by chemical and/or genetic means).

Where a diphtheria antigen is included in the mixture it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the mixture will typically be present at a concentration of at least 1 μg/ml each. In general, the concentration of any given antigen will be sufficient to elicit an immune response against that antigen.

As an alternative to using proteins antigens in the mixture, nucleic acid encoding the antigen may be used. Protein components of the mixture may thus be replaced by nucleic acid (preferably DNA e.g. in the form of a plasmid) that encodes the protein.

Multivalent Saccharide Vaccines

The invention also provides vaccines and immunogenic compositions comprising capsular saccharides from at least two (i.e. 2, 3 or 4) of serogroups A, C, W135 and Y of *N. meningitidis*, wherein said capsular saccharides are conjugated to carrier protein(s) and/or are oligosaccharides. Where the vaccine has only two conjugated oligosaccharides or polysaccharides from serogroups A, C, W135 and Y, these are preferably not from serogroups A and C (cf refs. 6, 119 & 120). Preferred compositions comprise saccharides from serogroups C and Y. Other preferred compositions comprise saccharides from serogroups C, W135 and Y.

The invention provides an immunogenic composition comprising a serogroup A oligosaccharide conjugate and a serogroup C oligosaccharide conjugate, and further comprising (i) an aluminium phosphate or an aluminium hydroxide adjuvant and (ii) a buffer. Where the composition comprises an aluminium phosphate adjuvant, the buffer is preferably a phosphate buffer; where it comprises an aluminium hydroxide adjuvant, the buffer is preferably a histidine buffer.

Where the vaccine comprises capsular saccharide from serogroup A, it is preferred that the serogroup A saccharide is combined with the other saccharide(s) shortly before use, in order to minimise its hydrolysis (cf. Hib saccharides). This can conveniently be achieved by having the serogroup A component in lyophilised form and the other serogroup component(s) in liquid form, with the liquid component being used to reconstitute the lyophilised component when ready for use. The liquid component preferably comprises an aluminium salt adjuvant, whereas the lyophilised serogroup A component may or may not comprise an aluminium salt adjuvant.

Thus the invention provides a kit comprising: (a) capsular saccharide from N. meningitidis serogroup A, in lyophilised form; and (b) capsular saccharide(s) from one or more (e.g. 1, 2, 3) of N. meningitidis serogroups C, W135 and Y, in liquid form. The saccharides are preferably conjugated to carrier protein(s) and/or are oligosaccharides. The kit may take the form of two vials.

The invention also provides a method for preparing a vaccine composition of the invention, comprising mixing a lyophilised capsular saccharide from N. meningitidis serogroup A with capsular saccharide(s) from one or more (e.g. 1, 2, 3) of N. meningitidis serogroups C, W135 and Y, wherein said one or more saccharides are in liquid form.

The invention also provides a kit comprising: (a) conjugated capsular oligosaccharide from N. meningitidis serogroup A, in lyophilised form; and (b) one or more further antigens in liquid form. The further antigen may or may not be conjugated capsular oligosaccharide from N. meningitidis serogroup C.

Immunogenic Compositions and Vaccines

Polysaccharides, oligosaccharides and conjugates of the invention are particularly suited to inclusion in immunogenic compositions and vaccines. A process of the invention may therefore include the step of formulating the polysaccharide, oligosaccharide or conjugate as an immunogenic composition or vaccine. The invention provides a composition or vaccine obtainable in this way.

Immunogenic compositions and vaccines of the invention will, in addition to the meningococcal saccharides, typically comprise 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose [121], lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in ref. 122.

Immunogenic compositions used as vaccines comprise an immunologically effective amount of saccharide antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine may be administered in conjunction with other immunoregulatory agents.

The vaccine may be administered in conjunction with other immunoregulatory agents.

The vaccine may include an adjuvant. Preferred adjuvants to enhance effectiveness of the composition include, but are not limited to: (1) aluminium salts (alum), such as aluminium hydroxides (including oxyhydroxides), aluminium phosphates (including hydroxyphosphates), aluminium sulfate, etc [Chapters 8 & 9 in ref. 123]; (2) oil-in-water emulsion formulations (with or without other specific immunostimulating agents such as muramyl peptides [Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.] or bacterial cell wall components), such as for example (a) MF59™[Chapter 10 in ref. 123; 124, 125], containing 5% Squalene, 0.5% TWEEN®80 (polyoxyethylenesorbitan, monooleate), and 0.5% SPAN®85 (sorbitan trioleate) (optionally containing MTP-PE) formulated into submicron particles using a microfluidizer, (b) SAF, containing 10% Squalane, 0.4% TWEEN®80 (polyoxyethylenesorbitan, monooleate), 5% PLURONIC™ L121 (block copolymer of propylene oxide and ethylene oxide), and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN®80 (polyoxyethylenesorbitan, monooleate), and one or more bacterial cell wall components from the group consisting of monophosphorylipid A (MPL), trehalose dimycolate (TDM), and cell wall skeleton (CWS), preferably MPL+ CWS (DETOX™); (3) saponin adjuvants [chapter 22 of ref. 123], such as QS21 or STIMULON™ (Cambridge Bioscience, Worcester, Mass.), either in simple form or in the form of particles generated therefrom such as ISCOMs (immunostimulating complexes; chapter 23 of ref. 123), which ISCOMS may be devoid of additional detergent e.g. ref. 126; (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12 [127], etc.), interferons (e.g. gamma interferon), macrophage colony stimulating factor (M-CSF), tumor necrosis factor (TNF), etc.; (6) monophosphoryl lipid A (MPL) or 3-O-deacylated MPL (3dMPL) e.g. refs. 128 & 129, optionally in the substantial absence of alum when used with pneumococcal saccharides e.g. ref. 130; (7) combinations of 3dMPL with, for example, QS21 and/or oil-in-water emulsions e.g. refs. 131, 132 & 133; (8) oligonucleotides comprising CpG motifs (Roman et al., *Nat. Med.*, 1997, 3, 849-854; Weiner et al., *PNAS USA*, 1997, 94, 10833-10837; Davis et al., *J. Immunol.*, 1998, 160, 870-876; Chu et al., *J. Exp. Med.*, 1997, 186, 1623-1631; Lipford et al., *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; International patent applications WO96/02555, WO98/16247, WO98/18810, WO98/40100, WO98/55495, WO98/37919 and WO98/52581) i.e. containing at least one CG dinucleotide, with 5-methylcytosine optionally being used in place of cytosine; (8) a polyoxyethylene ether or a polyoxyethylene ester e.g. ref. 134; (9) a polyoxyethylene sorbitan ester surfactant in combination with an octoxynol [135] or a polyoxyethylene alkyl ether or ester surfactant in combination with at least one additional non-ionic surfactant such as an octoxynol [136]; (10) a saponin and an immunostimulatory oligonucleotide (e.g. a CpG oligonucleotide) [137]; (11) an immunostimulant and a particle of metal salt e.g. ref. 138; (12) a saponin and an oil-in-water emulsion e.g. ref. 139; (13) a saponin (e.g. QS21)+3dMPL+IL-12 (optionally+a sterol) e.g. ref. 140; (14) *E. coli* heat-labile enterotoxin ("LT"), or detoxified mutants thereof, such as the K63 or R72 mutants [e.g Chapter 5 of ref. 141]; (15) cholera toxin ("CT"), or detoxified mutants thereof [e.g. Chapter 5 of ref. 141]; (16) liposomes [chapters 13 & 14 of ref. 123]; (17) chitosan [e.g. ref. 142]; (18) double-stranded RNA; (19) microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid) such as poly(lactide-co-glycolide), a polyhydroxybutyric acid, a polyorthoester, a polyanhydride, a polycaprolactone etc.). optionally treated to have a negatively-charged surface (e.g. with SDS) or a positively-charged surface (e.g. with a cationic detergent, such as CTAB); or (20) other substances that act as immunostimulating agents to enhance the effectiveness of the composition [e.g. chapter 7 of ref. 123].

Aluminium salts (especially aluminium phosphates and/or hydroxides) and MF59™ are preferred for use with the saccharide antigens of the present invention. Where an aluminium phosphate it used, it is possible to adsorb one or more of the saccharides to the aluminium salt, but it is preferred not to adsorb the saccharides to the salt, and this is favoured by including free phosphate ions in solution (e.g. by the use of a phosphate buffer). Where an aluminium hydroxide is used, it is preferred to adsorb the saccharides to the salt. The use of aluminium hydroxide as adjuvant is particularly advantageous for saccharide from serogroup A.

It is possible in compositions of the invention to adsorb some antigens to an aluminium hydroxide but to have other antigens in association with an aluminium phosphate. For tetravalent *N. meningitidis* serogroup combinations, for example, the following permutations are available:

| Serogroup | Aluminium salt (H = a hydroxide; P = a phosphate) | | | | | | | | | | | | | | | |
|---|---|---|---|---|---|---|---|---|---|---|---|---|---|---|---|---|
| A | P | H | P | H | H | H | P | P | P | H | H | H | P | P | P | H |
| C | P | H | H | P | H | H | P | H | H | P | P | H | P | H | P | P |
| W135 | P | H | H | H | P | H | H | P | H | H | P | P | P | P | H | P |
| Y | P | H | H | H | H | P | H | H | P | P | H | P | H | P | P | P |

For trivalent *N. meningitidis* serogroup combinations, the following permutations are available:

| Serogroup | Aluminium salt (H = a hydroxide; P = a phosphate) | | | | | | | |
|---|---|---|---|---|---|---|---|---|
| C | P | H | H | H | P | P | P | H |
| W135 | P | H | H | P | H | P | H | P |
| Y | P | H | P | H | H | H | P | P |

Once formulated, the compositions of the invention can be administered directly to the subject. The subjects to be treated can be animals; in particular, human subjects can be treated. The vaccines are particularly useful for vaccinating children and teenagers. They may be delivered by systemic and/or mucosal routes.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications (e.g. see ref. 143), needles, and hypossprays. Dosage treatment may be a single dose schedule or a multiple dose schedule (e.g. including booster doses).

Vaccines of the invention are preferably sterile. They are preferably pyrogen-free. They are preferably buffered e.g. at between pH 6 and pH 8, generally around pH 7. Where a vaccine comprises an aluminium hydroxide salt, it is preferred to use a histidine buffer [144].

Vaccines of the invention may comprise detergent (e.g. a Tween, such as Tween 80) at low levels (e.g. <0.01%). Vaccines of the invention may comprise a sugar alcohol (e.g. mannitol) or trehalose e.g. at around 15 mg/ml, particularly if they are to be lyophilised.

Optimum doses of individual antigens can be assessed empirically. In general, however, saccharide antigens of the invention will be administered at a dose of between 0.1 and 100 μg of each saccharide per dose, with a typical dosage volume of 0.5 ml. The dose is typically between 5 and 20 μg per saccharide per dose. These values are measured as saccharide.

Vaccines according to the invention may either be prophylactic (i.e. to prevent infection) or therapeutic (i.e. to treat disease after infection), but will typically be prophylactic.

The invention provides a method of raising an immune response in a patient, comprising administering to a patient a vaccine according to the invention. The immune response is preferably protective against meningococcal disease, and may comprise a humoral immune response and/or a cellular immune response. The patient is preferably a child.

The method may raise a booster response, in a patient that has already been primed against N. meningitidis.

The invention also provides the use of a polysaccharide, oligosaccharide or conjugate of the invention in the manufacture of a medicament for raising an immune response in an animal. The medicament is preferably an immunogenic composition (e.g. a vaccine). The medicament is preferably for the prevention and/or treatment of a disease caused by a Neisseria (e.g. meningitis, septicaemia, gonorrhoea etc.), by H. influenzae (e.g. otitis media, bronchitis, pneumonia, cellulitis, pericarditis, meningitis etc.) or by pneumococcus (e.g. meningitis, sepsis, pneumonia etc). The prevention and/or treatment of bacterial meningitis is thus preferred.

Vaccines can be tested in standard animal models (e.g. see ref. 145).

The invention also provides a process for solubilising a precipitated bacterial capsular polysaccharide, wherein ethanol is used as a solvent.

DEFINITIONS

The term "comprising" means "including" as well as "consisting" e.g. a composition "comprising" X may consist exclusively of X or may include something additional e.g. X+Y.

The term "about" in relation to a numerical value x means, for example, x±10%.

BRIEF DESCRIPTION OF DRAWINGS

FIGS. 2 to 4 show IgG titres obtained in mice against oligosaccharide antigens: FIG. 2 shows results using serogroup A oligosaccharide; FIG. 3 shows results for serogroup Y; and FIG. 4 shows results for serogroup W135.

FIG. 5 shows post-II IgG titres obtained in mice with a mixture of oligosaccharide conjugates for serogroups A and C.

FIGS. 6 to 8 show IgG titres obtained in mice with a mixture of oligosaccharide conjugates for serogroups C, W135 and Y: FIG. 6 shows the anti-serogroup W135 responses; FIG. 7 shows anti-serogroup Y responses; and FIG. 8 shows anti-serogroup C responses.

FIG. 9 shows the anti-serogroup W135 responses; FIG. 10 shows anti-serogroup Y responses; and FIG. 11 shows anti-serogroup A responses.

FIG. 17 shows post-II IgG titres, split by IgG subclass, obtained in mice after immunisation with a tetravalent mixture of oligosaccharide conjugates.

MODES FOR CARRYING OUT THE INVENTION

A. Production and Purification of Meningococcal Polysaccharides

Meningococci of serogroups A, W135 and Y were grown in 500 ml flasks containing 150 ml of Franz A as medium, for 12 hours at 35±1° C. Agitation was set at 150 rpm using a 35 mm throw Shaker. 85 ml of the culture was then inoculated in 20 L fermentor containing Watson as medium.

After 18.5 hours (W135 and Y) or 16.5 hours (A), when OD=10 was reached, the fermentation was interrupted by adding 300 ml of formalin and then, after 2 hours of incubation, and the fermentor was cooled to 10° C. The supernatant was collected by centrifugation followed by filtration (0.22 µm), and ultrafiltration with a 30 kDa membrane.

The crude concentrated polysaccharide was then precipitated by addition of CTAB as a 100 mg/ml water solution. The volumes added are shown in the following table. After 12 hours at room temperature, the CTAB complexes were recovered by centrifugation. The CTAB complex was extracted by adding a 95% ethanol solution at room temperature for 16-20 hrs under vigorous stirring. The volume of ethanol added is shown in the following table:

| Serogroup | CTAB volume (ml) | Volume of 95% ethanol (litres per kg wet paste) |
| --- | --- | --- |
| A | 475 | 3.5 to 6 |
| W135 | 200 | 4 to 6 |
| Y | 650 | 3.4 |

The resulting suspensions were filtered through a CUNO 10 SP depth filter. The filtrate was recirculated through a CUNO ZETACARBON™ cartridge until $OD_{275nm}$<0.2. The Z carbon filtrate was then collected and filtered through a 0.22 µm filter. The polysaccharide was eventually precipitated from the ethanol phase by addition of a $CaCl_2$ 2M water solution (10-12 ml/l of EtOH final solution). The purified polysaccharide was then collected by centrifugation, washed with 95% ethanol and dried under vacuum.

Figure 1:
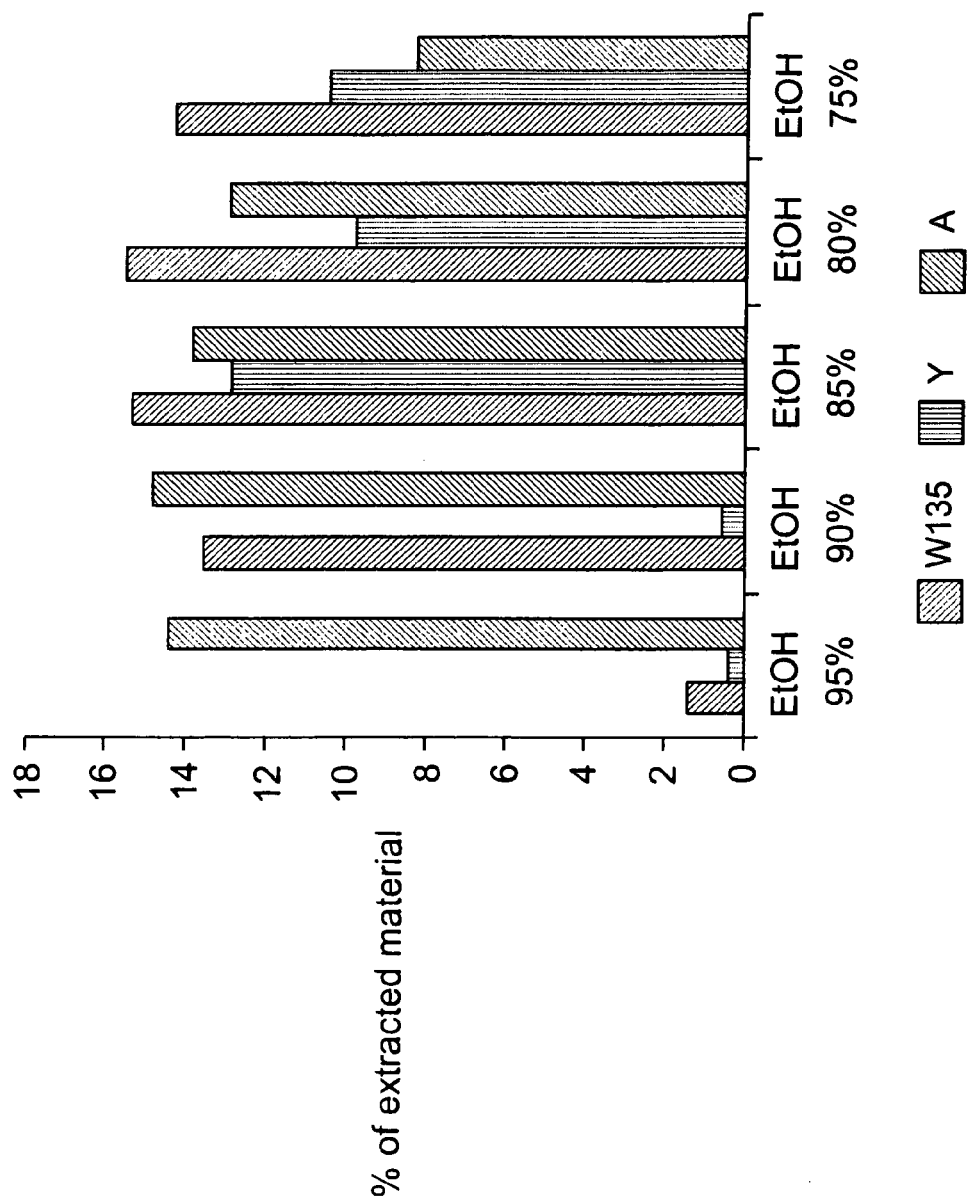
FIG. 1 shows the effect of varying ethanol:water ratios on polysaccharide solubilisation.

In other experiments, the final concentration of ethanol used for extraction was varied (FIG. 1). For serogroup A polysaccharide, a range of between 80 and 95% ethanol was most effective, with extraction efficiency decreasing at lower percentages. For serogroup W135, good extraction was achieved with between 75% and 90% ethanol, with 95% being less effective. For serogroup Y, the best results were achieved with between 75% and 85% ethanol, with higher percentages (e.g. 90%, 95%) being less effective. In general, it was noted that ethanol percentages below those reported here tended to increase the co-extraction of contaminants such as proteins. Ethanol percentages given in this paragraph are expressed as a final concentration (ethanol as percentage of total volume of ethanol+water) and are based on a water content in the CTAB-polysaccharide pastes recovered by centrifugation of about 50% (i.e. 500 g $H_2O$ per kg wet paste). This value was determined empirically in small scale-up experiments.

B. Conjugation of Serogroup A Polysaccharides a) Hydrolysis

The serogroup A meningococcal polysaccharide was hydrolysed in 50 mM sodium acetate buffer, pH 4.7 for about 3 hrs at 73° C. The hydrolysis was controlled in order to obtain oligosaccharides with an average degree of polymerisation (DP) of approximately 10, as determined by the (w/w) ratio between the total organic phosphorus and the monoester phosphate.

Figure 12:
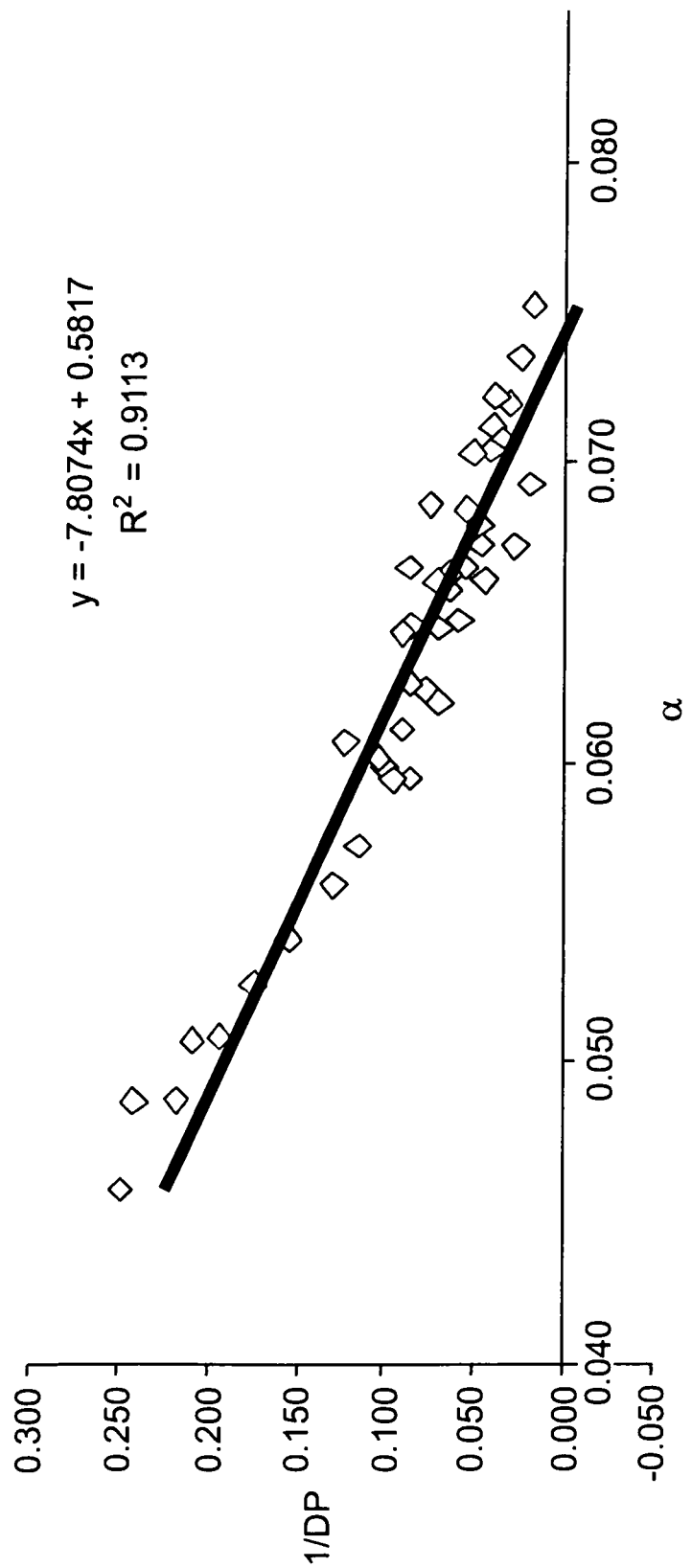
FIG. 12 is a calibration curve obtained using test MenA polysaccharide samples at different hydrolysis times. The curve shows the linear relationship between the reciprocal of the degree of polymerisation and optical rotatory power.

The DP ratio of (total organic phosphorus) to (phosphorus monoester) is inversely proportional to optical rotatory power ($\alpha$), as shown in FIG. 12. This relationship can be used to monitor the extent of hydrolysis more conveniently than direct phosphorus measurements.

b) Sizing

This step removes short-length oligosaccharides generated during the hydrolysis process. The hydrolysate obtained above was ultrafiltered through a 30 kDa cut-off membrane (12 diafiltration volumes of 5 mM acetate buffer, pH 6.5). The retentate, containing the high Mw species, was discarded; the permeate was loaded onto a onto a Q-Sepharose Fast Flow column equilibrated in acetate buffer 5 mM, pH 6.5. The column was then washed with 5 column volumes (CV) of equilibrating buffer, then with 10 CV of 5 mM acetate buffer/125 mM NaCl pH 6.5 in order to remove oligosaccharides with DP≤6. The sized oligosaccharide was then eluted with 5 CV of 5 mM acetate buffer/0.5 M NaCl pH 6.5.

The eluted oligosaccharide population has an average DP of about 15.

c) Introduction of a Primary Amino Group at the Reducing Terminus

Ammonium salt (acetate or chloride) was added to the sized oligosaccharide solution for a final concentration ranging from 49-300 g/L, then sodium-cyano-borohydride was added to a final concentration ranging from 12-73 g/L. After adjusting the pH to between 6-7.3, the mixture was incubated at 37° C. for 5 days.

The amino-oligosaccharides were then purified by tangential flow ultrafiltration with a 1 kDa or 3 kDa cut-off membrane using 13 diafiltration volumes of 0.5 M NaCl followed by 7 diafiltration volumes of 20 mM NaCl. The purified amino-oligosaccharide solution was analysed for phosphorus content (one chemical activity of the antigen) by the procedure of ref. 146 and the amount of introduced amino groups by the procedure of ref. 147.

The purified oligosaccharides were then dried with rotary evaporator to remove water.

d) Derivatisation to Active Ester

The dried amino-oligosaccharides were solubilised in distilled water at a 40 mM amino group concentration, then 9 volumes of DMSO were added followed by triethyl-amine at a final concentration of 200 mM. To the resulting solution, adipic acid N-hydroxysuccinimido diester was added for a final concentration of 480 mM.

The reaction was maintained under stirring at room temperature for 2 hours, then the activated oligosaccharide was precipitated with acetone (80% v/v final concentration). The precipitate was collected by centrifugation and washed several times with acetone to remove unreacted adipic acid N-hydroxysuccinimido diester and by-products. Finally the activated oligosaccharide was dried under vacuum.

The amount of active ester groups introduced into the oligosaccharide structure was determined by a colorimetric method as described in ref. 148.

e) Conjugation to $CRM_{197}$

The dried activated oligosaccharide was added to a 45 mg/ml solution of $CRM_{197}$ in 0.01M phosphate buffer pH 7.2 for an active ester/protein (mole/mole) ratio of 12:1. The reaction was maintained under stirring at room temperature overnight. After this period, the conjugate was purified by hydrophobic chromatography or tangential flow ultrafiltration. The purified MenA-$CRM_{197}$ conjugate was sterile filtered and stored at −20° C. or −60° C. until vaccine formulation.

The conjugate was analysed for: protein content (microBCA Protein Assay), MenA saccharide content (colorimetric analysis of phosphorus), free saccharide content, HPLC profile (on TSKgel G4000SW 7.5 mm ID×30 cm), and SDS-PAGE. Characteristics of typical preparations are shown in the following table:

| Lot Code | Saccharide (mg/ml) | protein (mg/ml) | Glycosylation | KD |
|---|---|---|---|---|
| 210201/A | 0.257 | 0.864 | 0.3 | 0.489 |
| 210201/BS | 0.308 | 1.354 | 0.23 | 0.503 |
| 210201/BL | 0.28 | 1.482 | 0.19 | 0.501 |
| 35I230595 | 0.138 | 0.3 | 0.46 | |
| 010900 | 0.092 | 0.337 | 0.27 | |
| DP29 | 0.105 | 0.245 | 0.43 | |
| A1 (UNSIZED) | 0.08 | 0.291 | 0.27 | |
| A2 (SIZED) | 0.446 | 2.421 | 0.18 | |

C. Conjugation of Serogroup W135 Polysaccharides a) Hydrolysis

The group W meningococcal polysaccharide was hydrolysed in acetic 50 mM sodium acetate buffer, pH 4.7 for about 3 hours at 80° C. This resulted in oligosaccharides with an average DP of about 15 to 20 as determined by ratio between sialic acid (SA) and reduced terminal SA.

Figure 13:
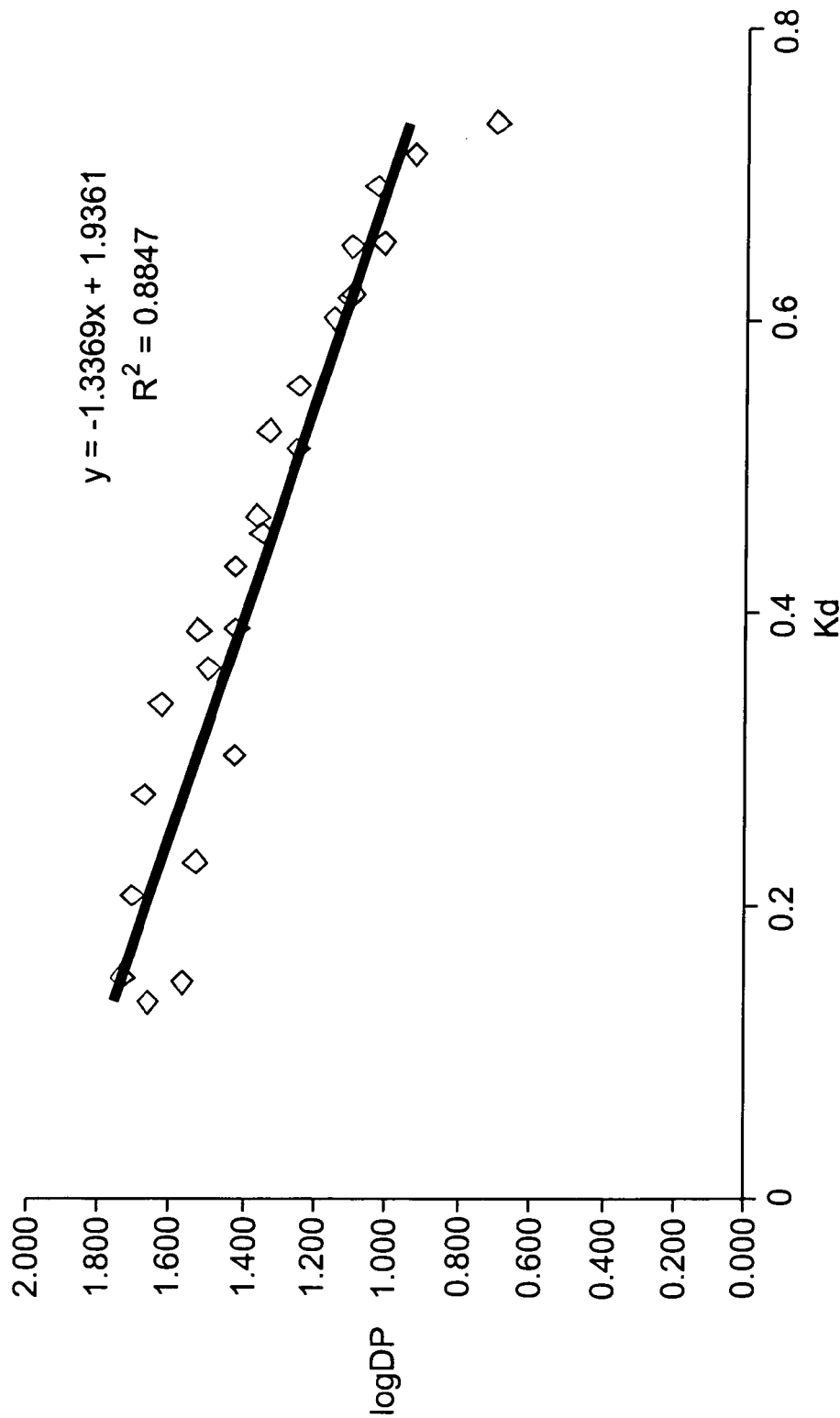
FIG. 13 is a calibration curve obtained using test MenY polysaccharide samples at different hydrolysis times. The curve shows the linear relationship between the log of the degree of polymerisation and KD (distribution coefficient).

The DP ratio of (total SA) to (reduced terminal SA) is related to the KD of the as determined by HPLC-SEC, as shown in FIG. 13. This relationship can be used to monitor the extent of hydrolysis more conveniently than direct SA measurements.

b) Sizing

The hydrolysate was ultrafiltered through a 30 kDa cut-off membrane (12 to 20 diafiltration volumes of 5 mM acetate buffer/15-30 mM NaCl pH 6.5). The retentate, containing the high MW species, was discarded while the permeate was loaded onto a Q-Sepharose Fast Flow column equilibrated in 5 mM acetate buffer/15 mM NaCl pH 6.5. The column was then washed with 10 CV equilibrating buffer, in order to remove oligosaccharides with DP≤3-4 and eluted with 3 CV 5 mM acetate buffer/500 mM NaCl pH 6.5.

c) Introduction of a Primary Amino Group at the Reducing Terminus

Ammonium chloride or ammonium acetate was added to the sized oligosaccharide solution to a final concentration of 300 g/L, then sodium-cyano-borohydride was added to 49 g/L or 73 g/L final concentration. The mixture was incubated at 50° C. for 3 days.

The amino-oligosaccharides were then purified by tangential flow ultrafiltration as described for serogroup A. The purified material was analysed for its content of sialic acid (colorimetric method according to ref. 149 and/or galactose (HPLC) (chemical activities of the MenW135 antigen). The purified oligosaccharides were then dried with rotary evaporator to remove water.

d) Derivatisation to Active Ester

The dried amino-oligosaccharides were derivatised as described above for serogroup A.

e) Conjugation to $CRM_{197}$

Conjugation was performed as described above for serogroup A but, to purify the conjugate, diafiltration with a 30 kDa membrane was used (50 diafiltration volumes of 10 mM phosphate buffer, pH 7.2). The purified conjugate was sterile filtered and stored at −20° C. or −60° C. until vaccine formulation.

The conjugate was analysed for the same parameters as described above for serogroup A. MenW saccharide content was assayed by colorimetric sialic acid determination:

| Lot code | saccharide (mg/ml) | protein (mg/ml) | Glycosylation | KD |
|---|---|---|---|---|
| lot 1 | 5.73 | 3.52 | 1.63 | 0.296 |
| lot 2/4, 5 | 3.51 | 2.88 | 1.22 | 0.308 |
| lot 3S | 2.49 | 2.25 | 1.11 | 0.380 |
| lot 3Sd | 2.03 | 2.24 | 0.91 | 0.394 |
| lot 3L | 2.32 | 2.3 | 1.01 | 0.391 |
| lot 3Ld | 1.94 | 2.29 | 0.85 | 0.383 |
| Lot 3S/pr. Glic6 | 0.363 | 0.82 | 0.44 | 0.498 |
| Lot 3S/pr. Glic9 | 0.424 | 0.739 | 0.57 | 0.447 |
| Lot 3S/pr. Glic12 | 0.479 | 0.714 | 0.671 | 0.414 |

D. Conjugation of serogroup Y Polysaccharides a) Hydrolysis

The group Y meningococcal polysaccharide was hydrolysed as described above for serogroup W135. This gave oligosaccharides with an average DP of about 15 to 20 as determined by ratio between SA and reduced terminal SA (conveniently measured indirectly as described under C(a) above).

b) Sizing, c) Introduction of Amino Group, d) Derivatisation to Active Ester and e) Conjugation These steps were performed as described above for serogroup W135. The purified conjugate was sterile filtered and stored at −20° C. or −60° C. until vaccine formulation.

The conjugate was analysed in the same way as described above for serogroup W135:

| Lot Code | saccharide (mg/ml) | protein (mg/ml) | Glycosylation | KD |
|---|---|---|---|---|
| lot 1A | 1.16 | 0.92 | 1.26 | 0.303 |
| lot 1B | 4.57 | 3.55 | 1.29 | 0.339 |
| Lot 2/4, 5 | 2.32 | 6.1 | 0.38 | 0.467 |
| lot 2/6 | 1.75 | 5.73 | 0.3 | 0.498 |

E. Immunogenicity of Individual Conjugates

The frozen bulk conjugates were thawed. Each was diluted, under stirring, to a final concentration of 20 μg saccharide/ml, 5 mM phosphate, 9 mg/ml NaCl, aluminium phosphate (to give an $Al^{3+}$ concentration of 0.6 mg/ml), pH 7.2. The mixtures were then kept, without stirring, at 2-8° C. overnight and further diluted with saline to 4 μg saccharide/ml for mouse immunisation.

A second set of vaccines was prepared for each serogroup in the same way, but the addition of aluminium phosphate was replaced with same volume of water.

Ten Balb/c mice for each immunisation group were injected s.c. twice with 0.5 ml vaccine at weeks 0 and 4. Bleedings were performed before immunisation, the day before the second dose and 2 weeks after the second dose. Immunisations were performed with (a) the conjugate vaccine with or without alum, (b) saline control and (c) unconjugated polysaccharide control.

Specific anti-polysaccharide IgG antibodies were determined in the sera of immunised animals essentially as described in ref. 150. Each individual mouse serum was analysed in duplicate by a titration curve and GMT was calculated for each immunisation group. Titres were calculated in Mouse Elisa Units (MEU) using 'Titerun' software (FDA). Anti-polysaccharide titre specificity was determined by competitive ELISA with the relevant polysaccharide as competitor.

Figure 2:
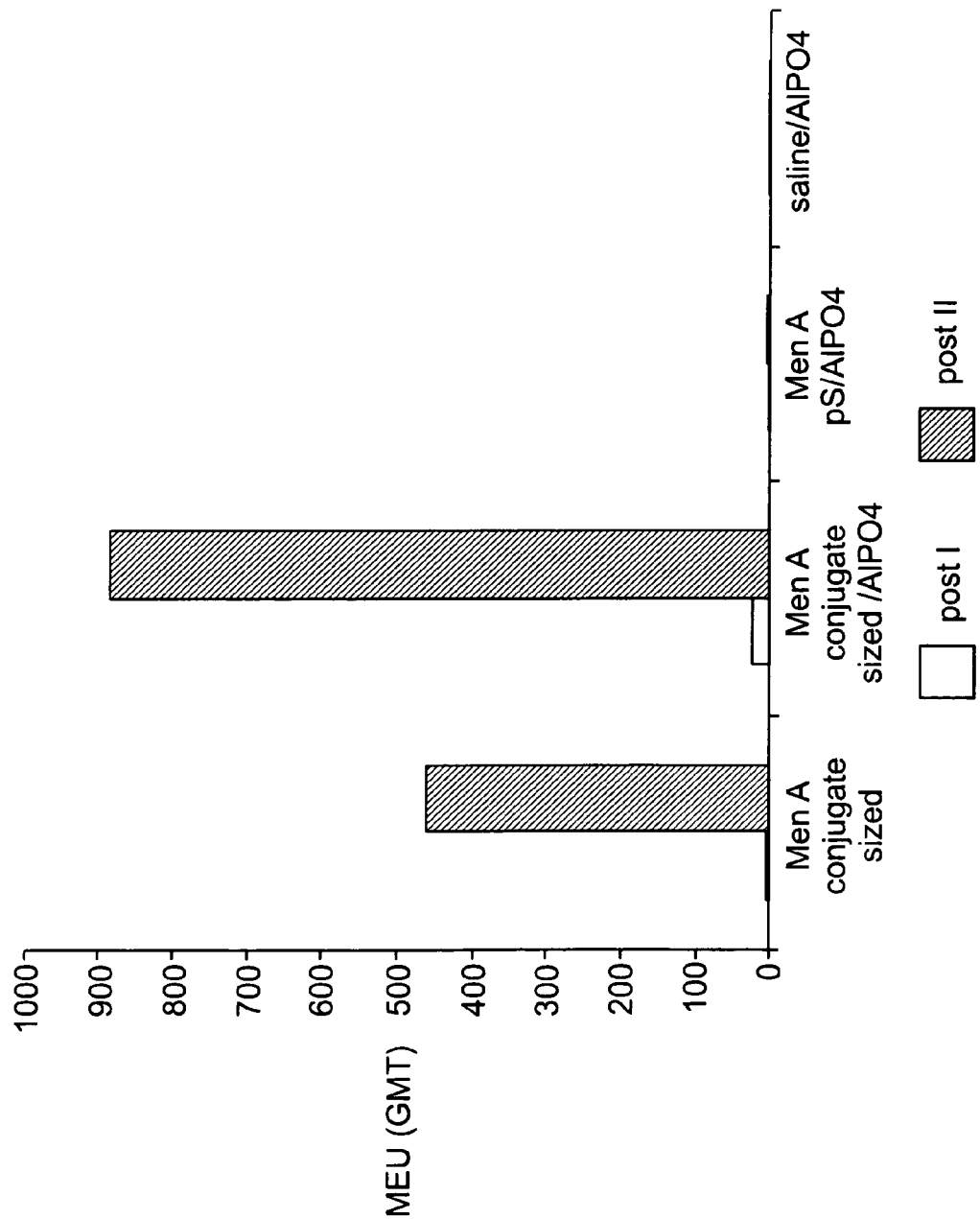
Figure 3:
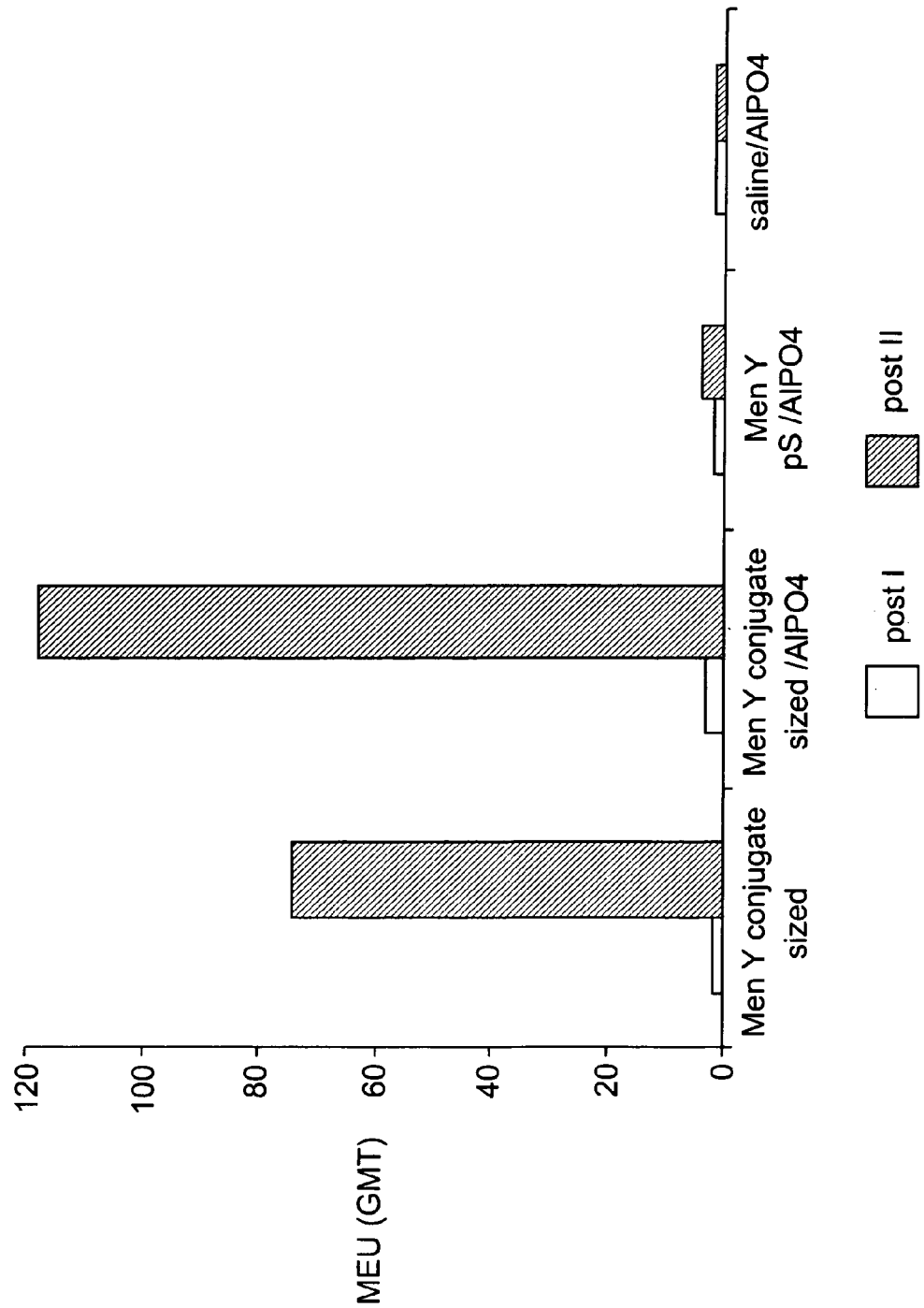

As shown in FIG. 2, the MenA conjugate induced high antibody titres in animals. As expected, the unconjugated polysaccharide was not immunogenic. The conjugate formulation with an aluminium phosphate as adjuvant induced a higher level of antibodies compared to the titre obtained by the conjugate alone. Similar results were seen for MenY (FIG. 3) and MenW135 (FIG. 4).

Figure 14:
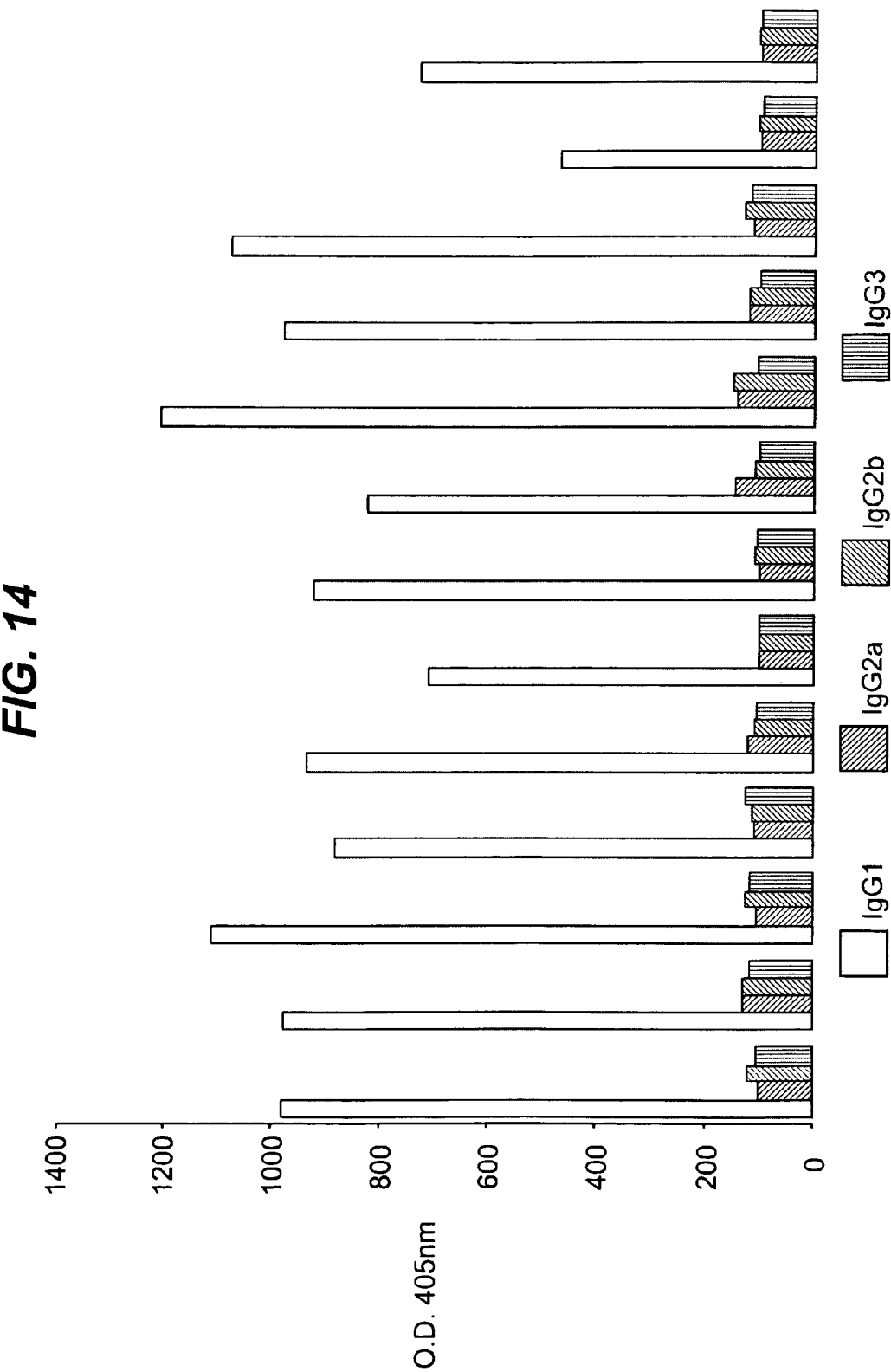
FIGS. 14 to 16 show post-II IgG titres, split by IgG subclass, obtained in mice after immunisation with oligosaccharide conjugates for serogroups: (14) A; (15) C; (16) W135 and (17) Y.
Figure 15:
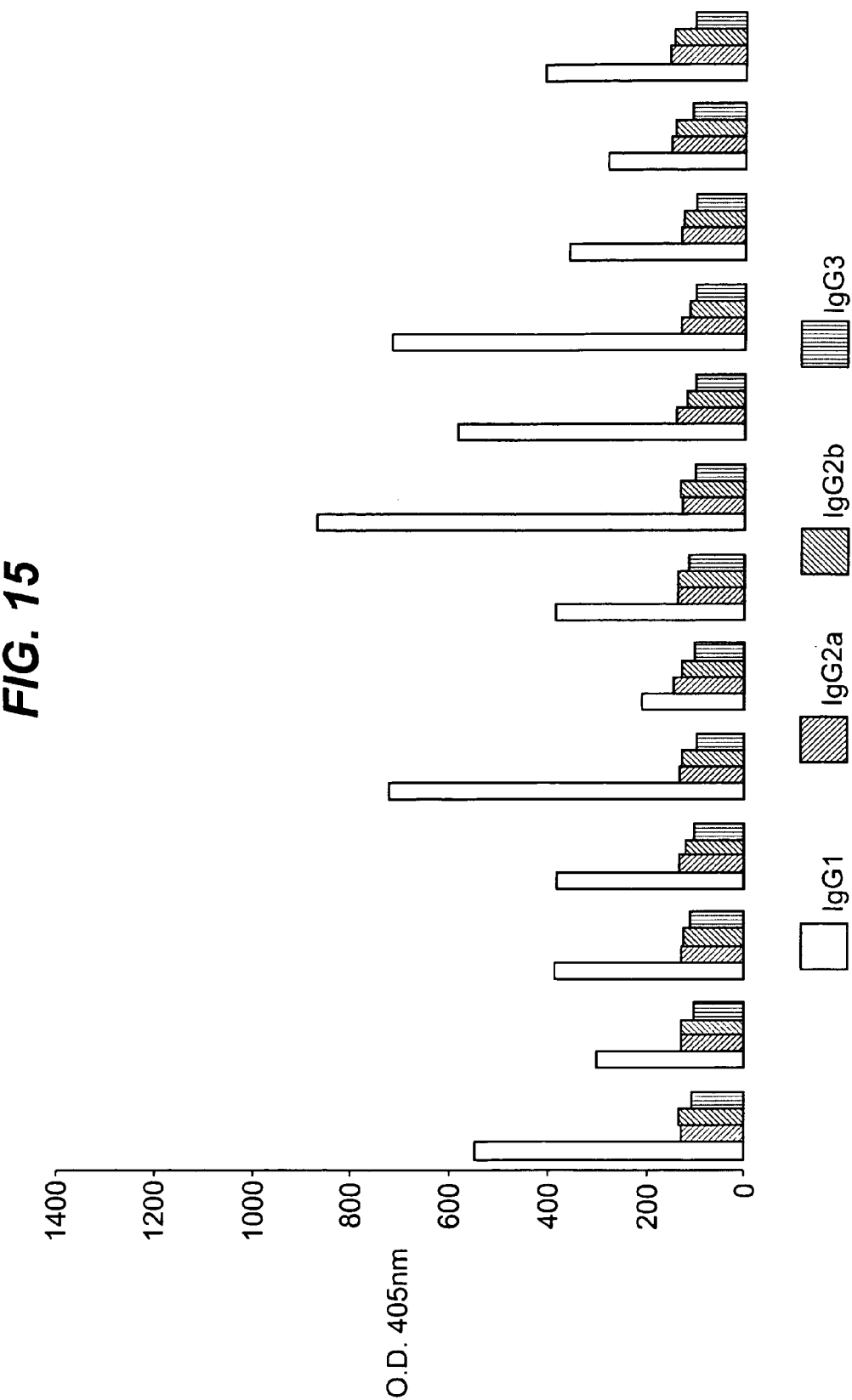
Figure 16:
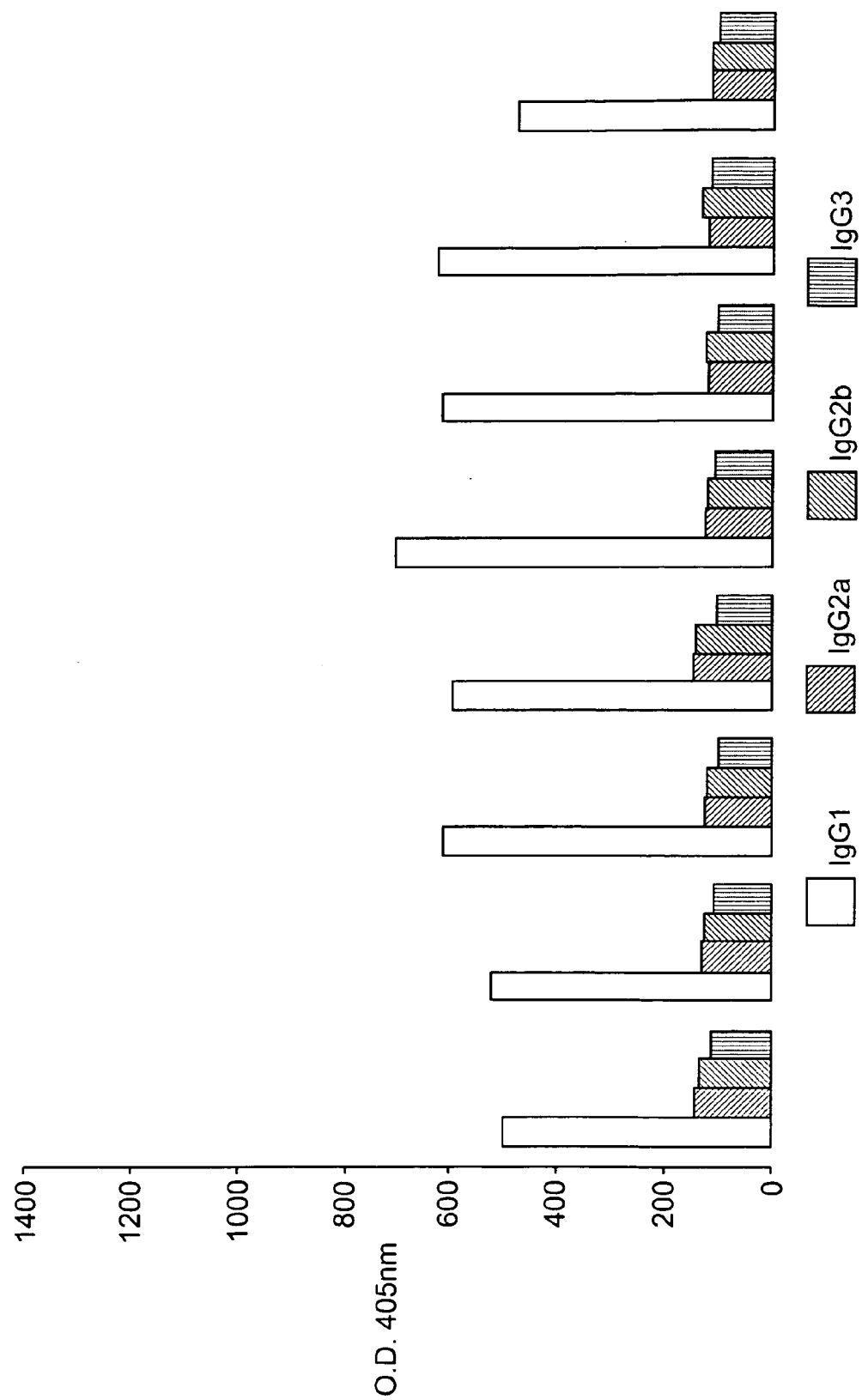
Figure 17A:
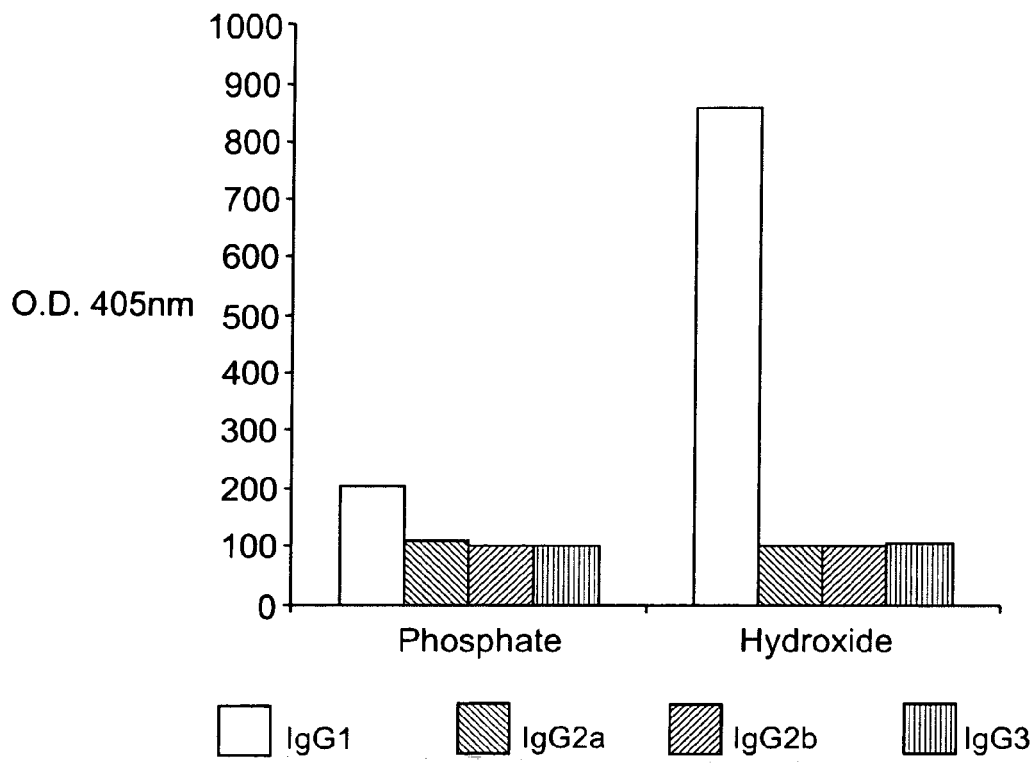
FIG. 17(A) shows the results of IgG subclass analysis for MenA.
Figure 17B:
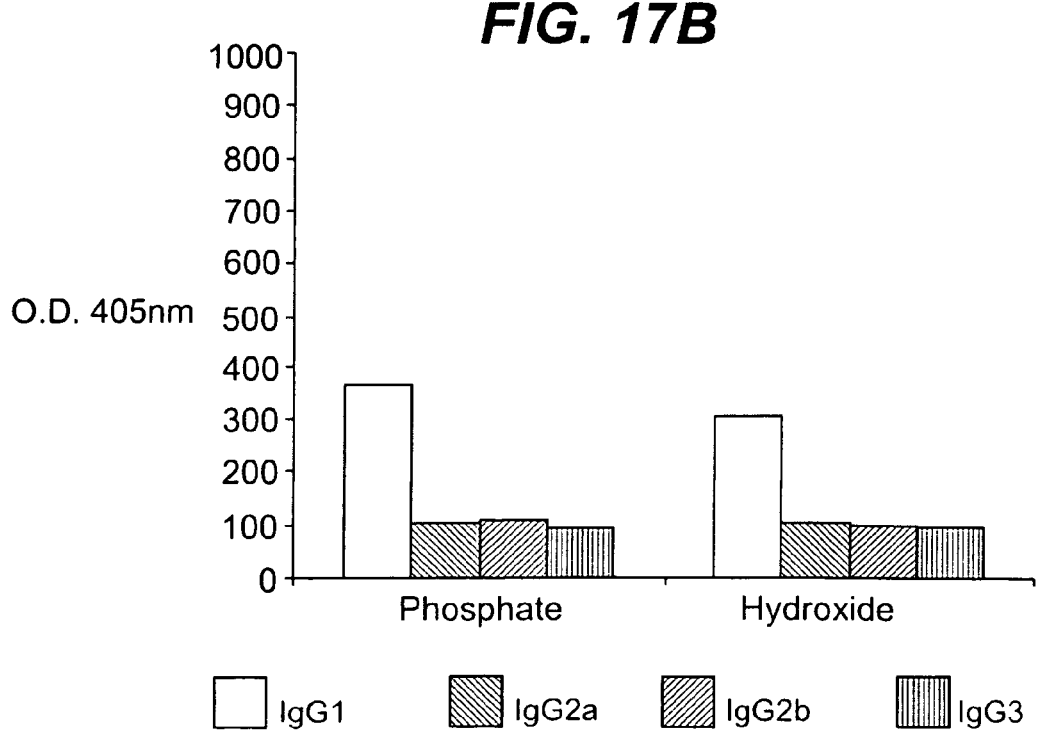
FIG. 17(B) shows the results of IgG subclass analysis for MenC.
Figure 17C:
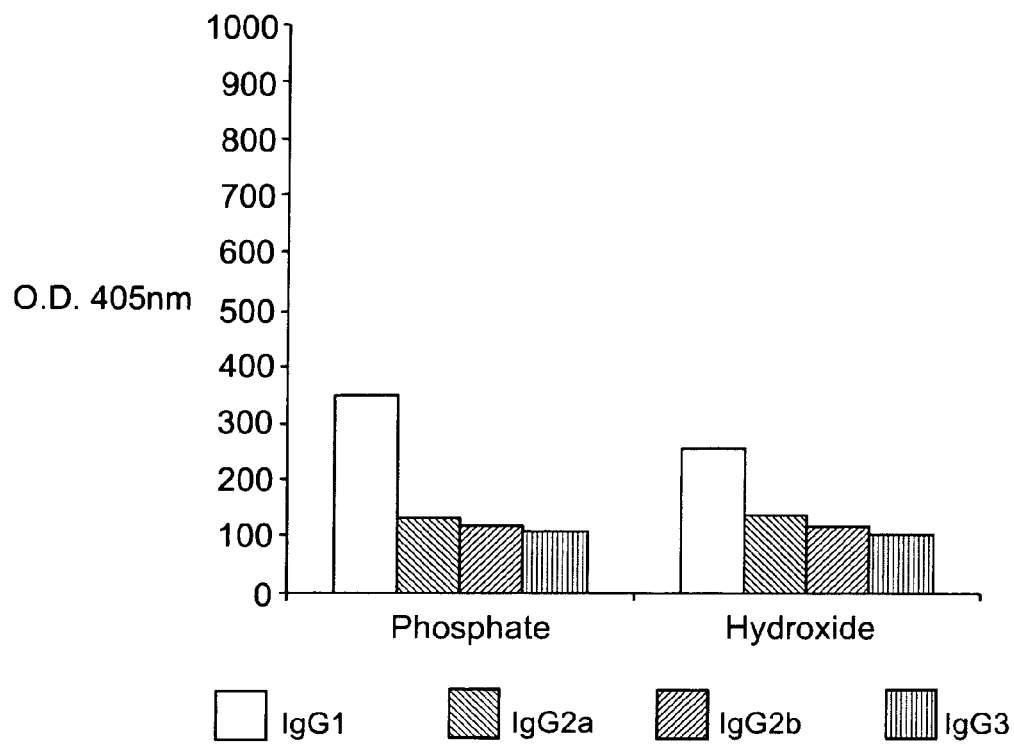
FIG. 17(C) shows the results of IgG subclass analysis for MenW135.
Figure 17D:
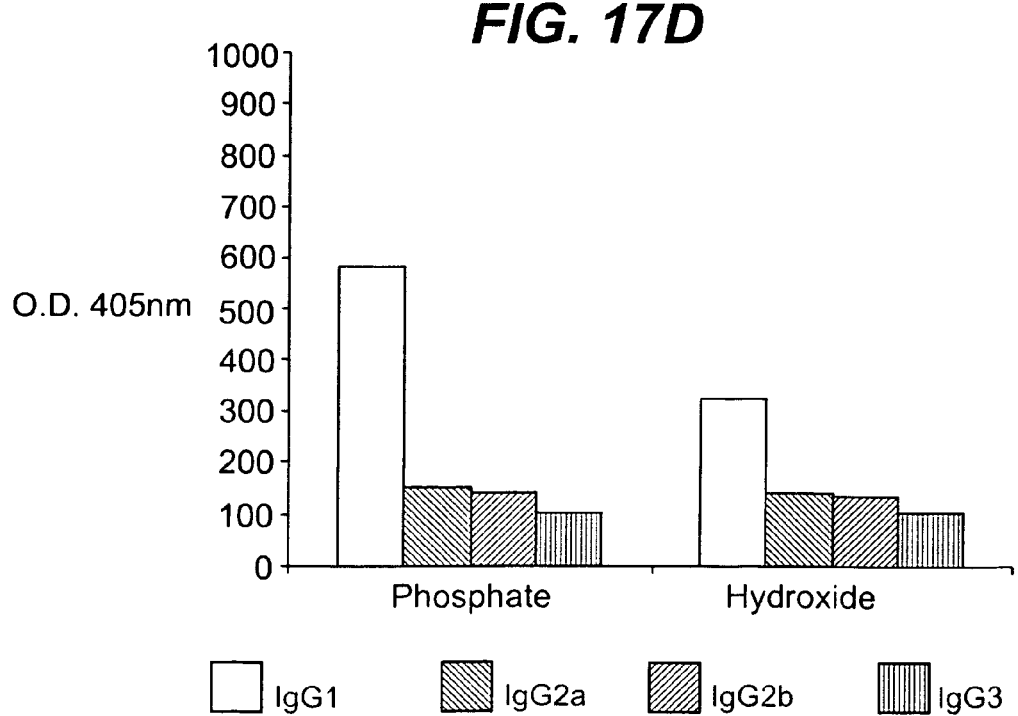
FIG. 17(D) shows the results of IgG subclass analysis for MenY.
Figure 18:
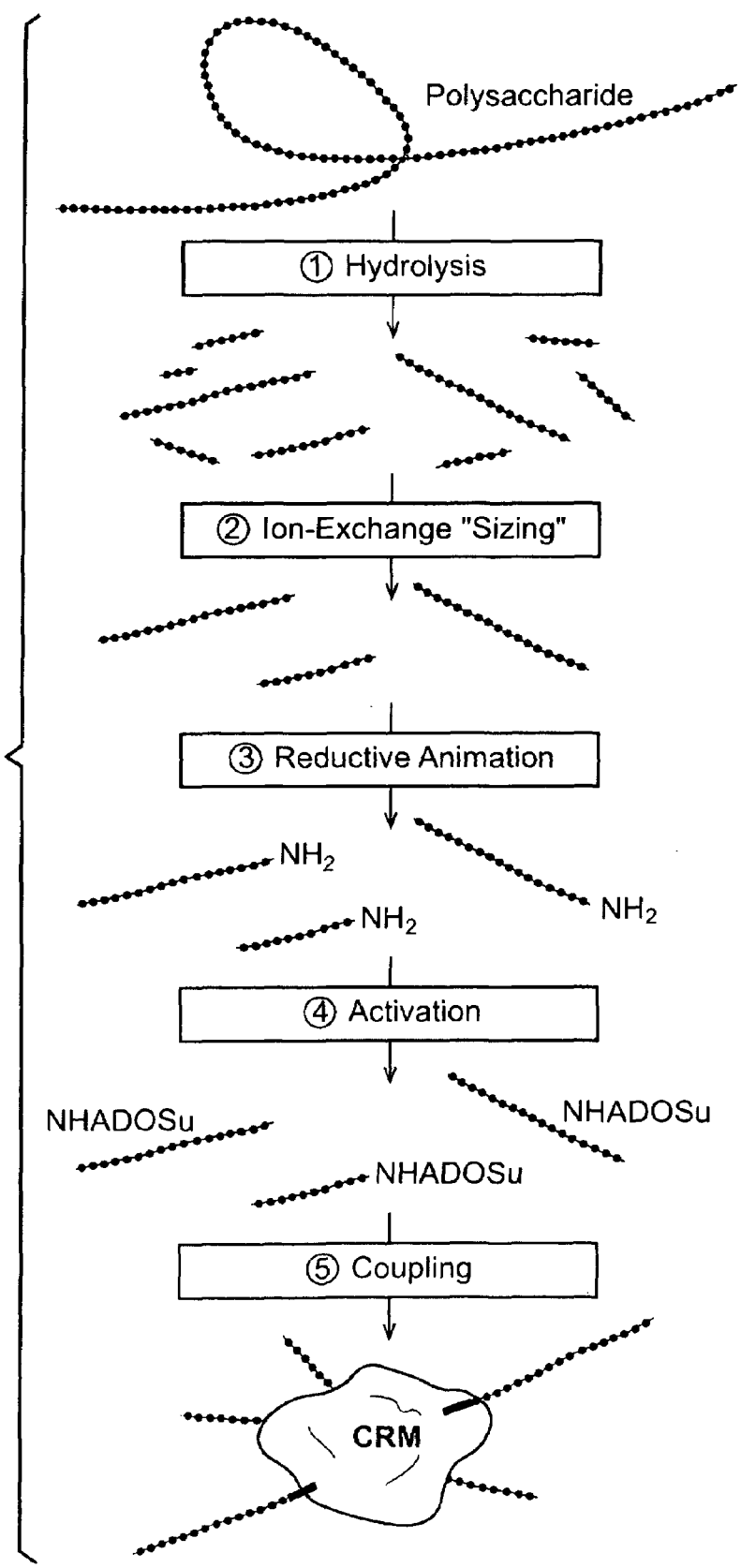
FIG. 18 illustrates the preparation of an oligosaccharide conjugate.

The IgG subclass of the post-II immune responses was measured for various groups. Specific subclasses were determined using the same ELISA method as used for the determination of the total IgG titer in section E above, but using alkaline phosphatase-anti mouse -IgG1, -IgG2a, -IgG2b or -IgG3 (Zymed) as the secondary antibody. Titres were expressed as $OD_{405nm}$ obtained after 30 minutes of substrate development using serum diluted 1:3200, and are shown in FIGS. 14 (MenA), 15 (MenW135) and 16 (MenY). Responses are primarily in subclass IgG1, which is the subclass predominantly induced in mice by T-dependent antigens. Because polysaccharides are inherently T-independent antigens which are not able to induce immunological memory, these data show that conjugation has had the desired effect.

Post-II sera were also tested for bactericidal activity using an in vitro assay to measure complement-mediated lysis of bacteria. Post-II sera were inactivated for 30 minutes at 56° C. before the use in the assay, and 25% baby rabbit complement was used as source of complement. Bactericidal titre was expressed as the reciprocal serum dilution yielding 50% killing of bacteria against the following strains: MenA G8238, A1, F6124; MenW135 5554(OAc+) and 242317 (OAc−); MenY 242975(OAc−) and 240539(OAc+).

Results for MenA included:

| Carrier | Poly/oligo saccharide | Approx. αDP | Aluminium adjuvant | GMT | Bactericidal activity |
|---|---|---|---|---|---|
| $CRM_{197}$ | O | 15 | — | 461 | F8238: 2048-4096; F6124: 2048-4096 |
| $CRM_{197}$ | O | 15 | phosphate | 920 | F8238: 4096; F6124: 4096 |
| — | P | — | phosphate | 3 | F8238: 8; F6124: 128 |
| $CRM_{197}$ | O | 15 | — | 290 | F8238: 512-1024 |
| — | P | — | — | 2 | F8238: <4 |

-continued

| Carrier | Poly/oligo saccharide | Approx. αDP | Aluminium adjuvant | GMT | Bactericidal activity |
|---|---|---|---|---|---|
| $CRM_{197}$ | O | 15 | — | 155 | F8238: 512-1024 |
| $CRM_{197}$ | O | 15 | — | 393 | F8238: 1024 |
| $CRM_{197}$ | O | 15 | — | 396 | — |
| $CRM_{197}$ | O | 15 | phosphate | 1396 | F8238: 4096 |
| $CRM_{197}$ | O | 15 | phosphate | 1461 | F8238: 2048-4096 |
| $CRM_{197}$ | O | 15 | phosphate | 1654 | F8238: 2048 |
| $CRM_{197}$ | O | 29 | phosphate | 1053 | F8238: 2048 |
| $CRM_{197}$ | unsized O | 10 | phosphate | 1449 | F8238: 2048 |
| $CRM_{197}$ | O | 15 | phosphate | 626 | F8238: 2048-4096 |
| $CRM_{197}$ | O | 15 | — | 742 | — |
| $CRM_{197}$ | O | 15 | — | 2207 | — |
| $CRM_{197}$ | O | 29 | — | 1363 | — |
| $CRM_{197}$ | unsized O | 10 | — | 615 | — |
| $CRM_{197}$ | O | 15 | phosphate | 1515 | — |
| $CRM_{197}$ | O | 15 | phosphate | 876 | — |
| $CRM_{197}$ | O | 15 | phosphate | 1232 | — |
| $CRM_{197}$ | O | 15 | phosphate | 852 | — |
| $CRM_{197}$ | O | 15 | phosphate | 863 | F8238: 2048; A1: 2048; F6124: >2048 |
| $CRM_{197}$ | O | 27 | phosphate | 1733 | F8238: 4096-8192; F6124: 4096-8192 |
| $CRM_{197}$ | O | 15 | phosphate | 172 | F8238: 1024; A1: 1024-2048; F6124: 2048 |
| $CRM_{197}$ | O | 15 | hydroxide | 619 | F8238: 1024; A1: 2048; F6124: 2048 |

Results for MenW135 included:

| Carrier | Poly/oligo saccharide | OAc | Aluminium adjuvant | GMT | Bactericidal activity |
|---|---|---|---|---|---|
| $CRM_{197}$ | O | + | — | 14 | 5554: 256-512 |
| $CRM_{197}$ | O | + | phosphate | 23 | 5554: 256-512 |
| — | P | — | — | — | 5554: 4 |
| $CRM_{197}$ | O | + | — | 45 | 5554: 1024 |
| $CRM_{197}$ | O | + | — | 101 | 5554: 64-128 |
| $CRM_{197}$ | O | + | — | 80 | 5554: 256-512 |
| $CRM_{197}$ | O | + | phosphate | 221 | 5554: 1024-2048; 242317: 1024-2048 |
| $CRM_{197}$ | O | − | — | 52 | 5554: 512-1024 |
| $CRM_{197}$ | O | − | phosphate | 329 | 5554: 1024-2048; 242317: 1024-2048 |
| $CRM_{197}$ | O | + | — | 41 | 5554: 256-512 |
| $CRM_{197}$ | O | + | phosphate | 24 | 5554: 1024; 242317: 128-256 |
| $CRM_{197}$ | O | − | — | 116 | 5554: 256-512 |
| $CRM_{197}$ | O | − | phosphate | 185 | 5554: 1024; 242317: 512-1024 |
| $CRM_{197}$ | O | + | phosphate | 565 | 5554: 2048 |
| $CRM_{197}$ | O | + | phosphate | 328 | 5554: 512-1024 |
| $CRM_{197}$ | O | + | phosphate | 490 | 5554: 1024-2048 |
| $CRM_{197}$ | O | + | hydroxide | 189 | 5554: 512-1024; 242317: 512-1024 |
| $CRM_{197}$ | O | + | phosphate | 80 | 5554: 512-1024; 242317: 512-1024 |
| $CRM_{197}$ | O | + | hydroxide | 277 | 5554: 512-1024; 242317: 1024-2048 |

Results for MenY included:

| Carrier | Poly/oligo saccharide | αDP | Aluminium adjuvant | GMT | Bactericidal activity |
|---|---|---|---|---|---|
| $CRM_{197}$ | O | >15 | — | 751 | 242975: 8192 |
| $CRM_{197}$ | O | >15 | phosphate | 1190 | 242975: 8192-16384; 240539: 8192-16384 |
| $CRM_{197}$ | O | >15 | — | 284 | 242975: 2048-4096 |
| $CRM_{197}$ | O | >15 | phosphate | 775 | 242975: 2048-4096 |
| — | P | — | — | — | 242975: 256 |
| $CRM_{197}$ | O | >15 | — | 1618 | 242975: 4096-8192 |
| $CRM_{197}$ | O | >15 | — | 2123 | 242975: 2048 |
| $CRM_{197}$ | O | <10 | — | 253 | 242975: 512-1024 |
| $CRM_{197}$ | O | <10 | — | 1060 | 242975: 256-512 |
| $CRM_{197}$ | O | >15 | hydroxide | 1167 | 242975: 8192; 240539: 8192-16384 |
| $CRM_{197}$ | O | >15 | phosphate | 665 | 242975: 8192; 240539: 8192-16384 |
| $CRM_{197}$ | O | >15 | phosphate | 328 | 242975: 4096; 240539: 2048-4096 |
| $CRM_{197}$ | O | >15 | hydroxide | 452 | 242975: 2048; 240539: 1024-2048 |

F. Immunogenicity of MenA Conjugate in Combination with MenC Conjugate

CRM-MenC concentrated bulk (from Chiron Vaccines, Italy) was mixed with CRM-MenA concentrated bulk (obtained as described above) were diluted and mixed by stirring. Three different preparations were made. Each contained 20 μg saccharide/ml for MenA, but different amounts of MenC conjugate were included: (i) 20 μg saccharide/ml (ii) 10 μg saccharide/ml; (iii) 5 μg saccharide/ml. Ratios of MenA:MenC (w/w) were thus: (i) 1:1; (ii) 2:1; (iii) 4:1.

Each preparation also contained 5 mM sodium phosphate, 9 mg/ml NaCl, aluminium phosphate (to give an $Al^{3+}$ concentration of 0.6 mg/ml), pH 7.2. Each mixture was then kept, without stirring, at 2-8° C. overnight and further diluted 1:5 with saline before mice immunisation.

A second set of vaccines was prepared in the same way, but the addition of aluminium phosphate was replaced with same volume of water.

For each of the six vaccines, ten Balb/c mice were immunised as described above. Control groups received saline or MenA conjugate alone.

Anti-polysaccharide antibodies for MenA and MenC were determined as described above.

The results obtained with the mixture of MenA+MenC conjugates clearly indicate that the ratio (w/w) between A and C components plays a crucial role for MenA immunogenicity.

Figure 5A:
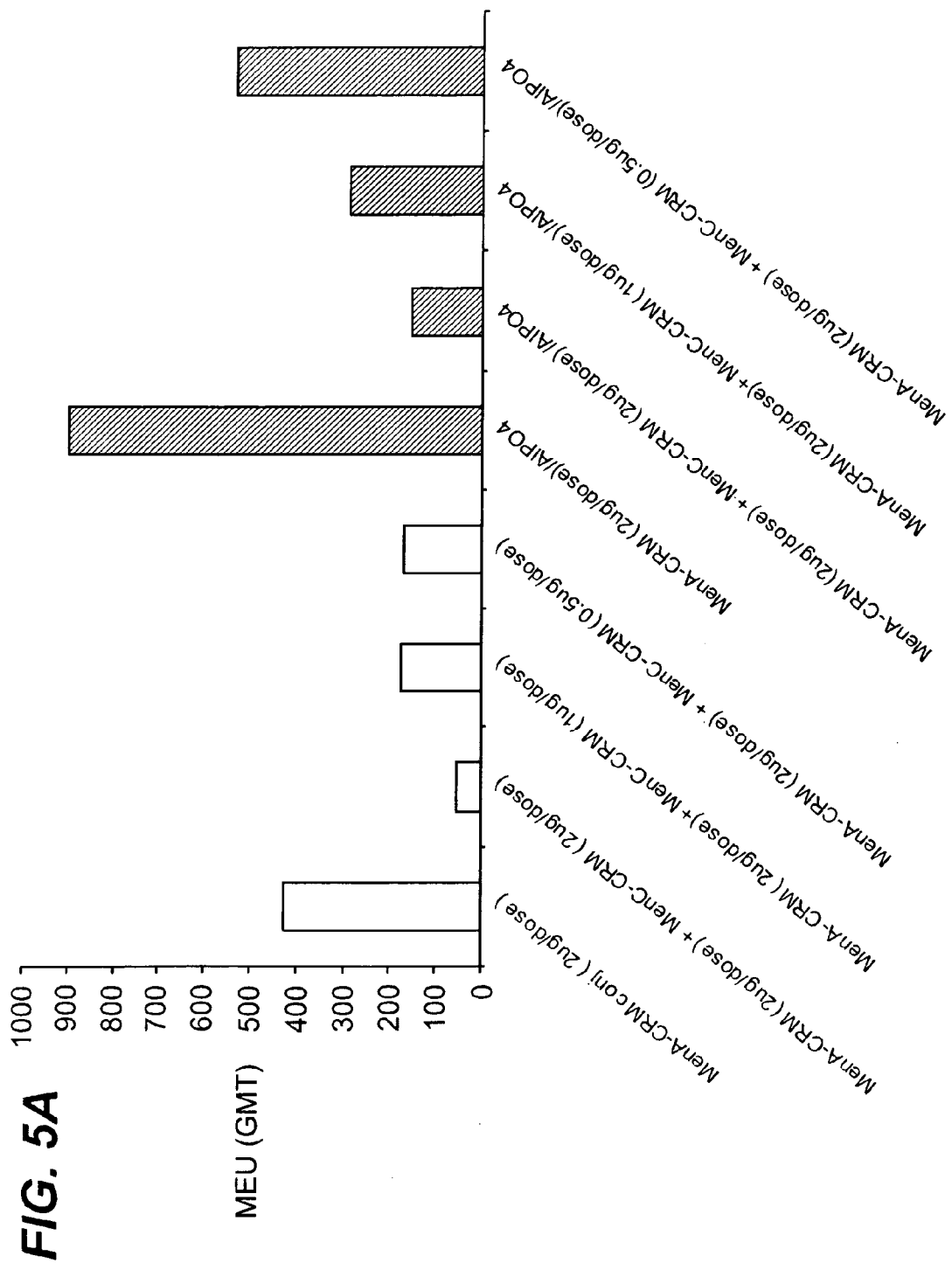
FIG. 5a shows the anti-serogroup A responses.
Figure 5B:
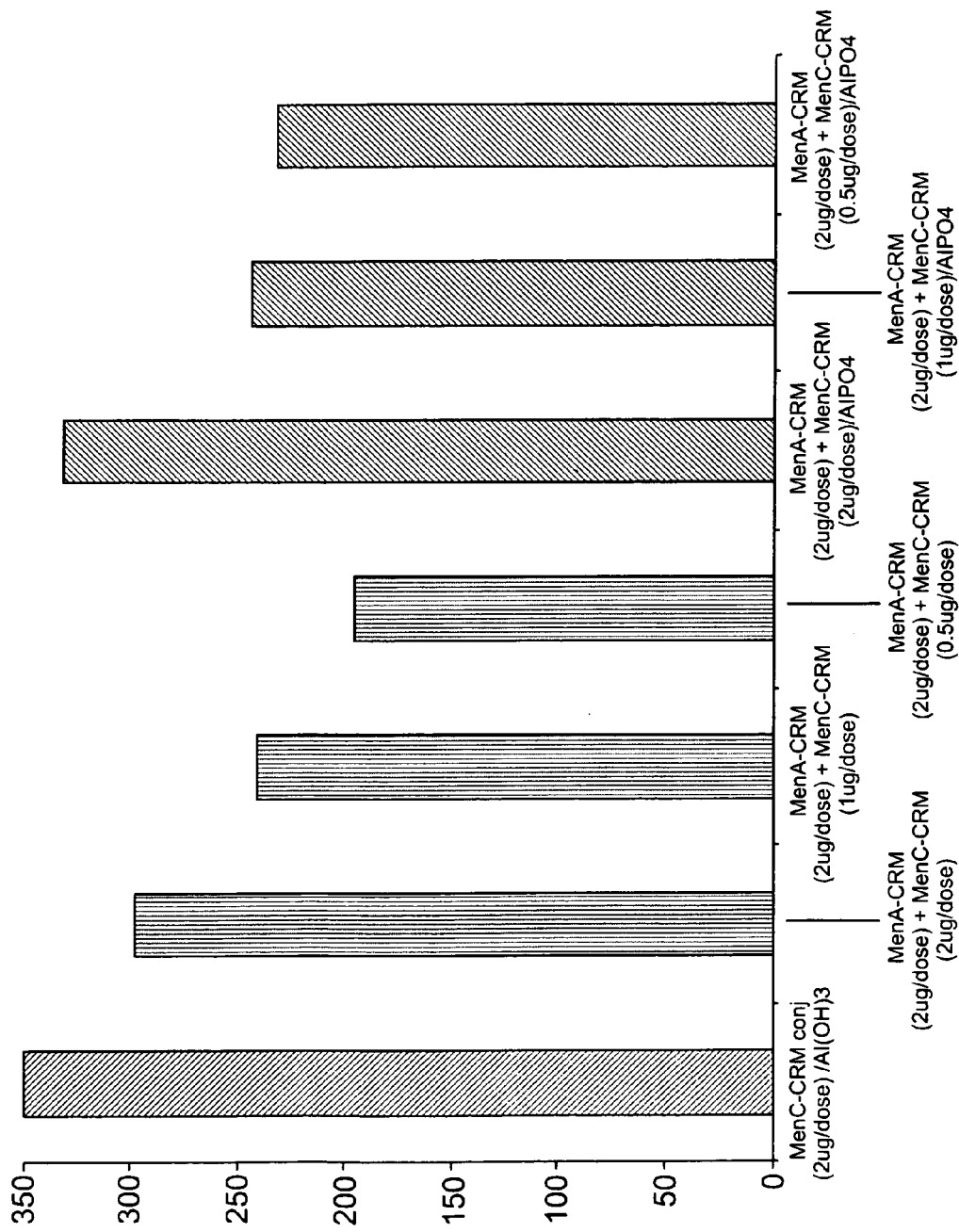
FIG. 5b shows anti-serogroup C responses.

The specific anti-MenApS titre obtained with the MenA conjugate control was higher (with or without alum adjuvant) than for the MenA+MenC combination at the same dosage (FIG. 5a). When a lower amount of MenC conjugate is used in the combination, a better anti-MenApS titre is induced by the MenA conjugate component. At the same time, the anti-MenC titre remains acceptable (FIG. 5b).

Experiments were also performed using a guinea pig model. Three different preparations were made, using the same aluminium phosphate adjuvant as before (amorphous hydroxyphosphate, $PO_4/Al$ molar ratio between 0.84 and 0.92, 0.6 mg $Al^{3+}$/ml):

| Preparation | Men A* | MenC* | MenA:MenC ratio |
|---|---|---|---|
| A | 20 μg/ml | 20 μg/ml | 1:1 |
| B | 40 μg/ml | 20 μg/ml | 2:1 |
| C | 20 μg/ml | 10 μg/ml | 1:½ |

*Expressed as saccharide

Figure 19A:
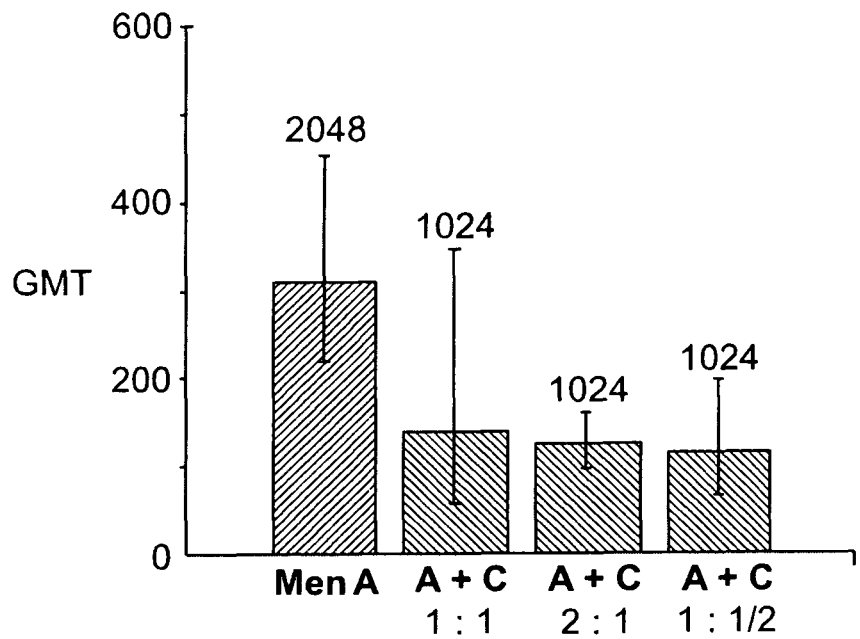
FIG. 19 shows (A) anti-MenA and (B) anti-MenC GMT (±95% confidence intervals) obtained in a guinea pig model. Values above bars are serum bactericidal assay (SBA) titres i.e. the reciprocal of the sera dilution yielding the 50% of killing.
Figure 19B:
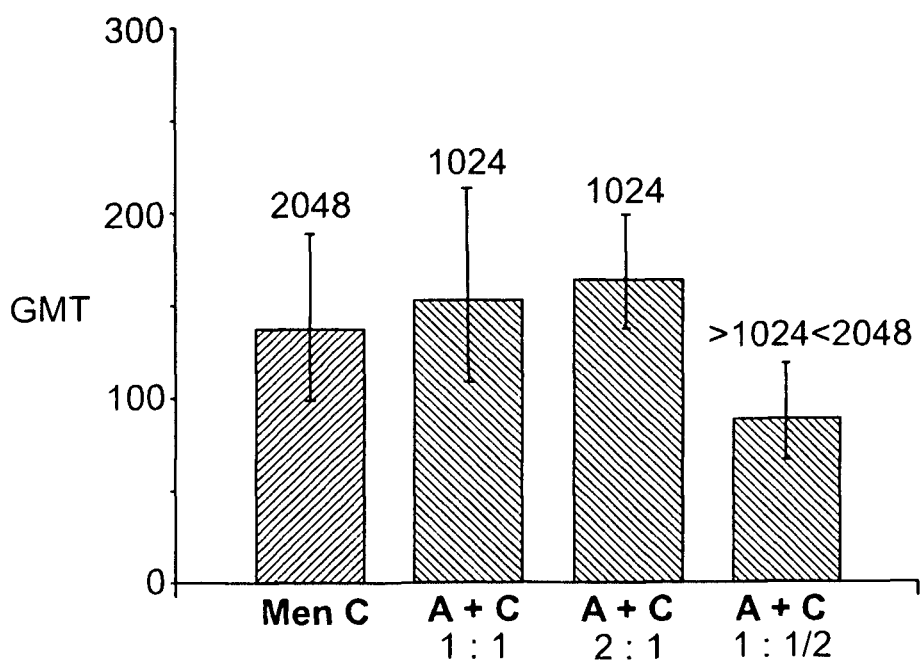

These preparations were diluted 1:2 with saline and used to immunise guinea pigs. Five guinea pigs (Hartelley strain, female, 450-500 grams) for each immunisation group were injected s.c. twice with 0.5 ml vaccine at days 0 and 28. Bleedings were performed before the first immunisation and then at day 42. Sera were stored at −70° C. prior to analysis by ELISA and serum bactericidal assay (against MenA strain MK 83/94 or .MenC strain C11). Results are shown in FIG. 19.

G. Combination Vaccine for Serogroups C, W135 and Y

Conjugates of polysaccharides from serogroups C, W135 and Y were mixed as described above to give a final concentration of 20 μg saccharide/ml for each conjugate. The vaccine contained a final concentration of 5 mM sodium phosphate and 9 mg/ml NaCl, pH 7.2. After overnight storage, the mixture was diluted to contain 4 μg saccharide/ml for each conjugate for immunisation.

Immunisations and analysis took place as before.

Figure 7:
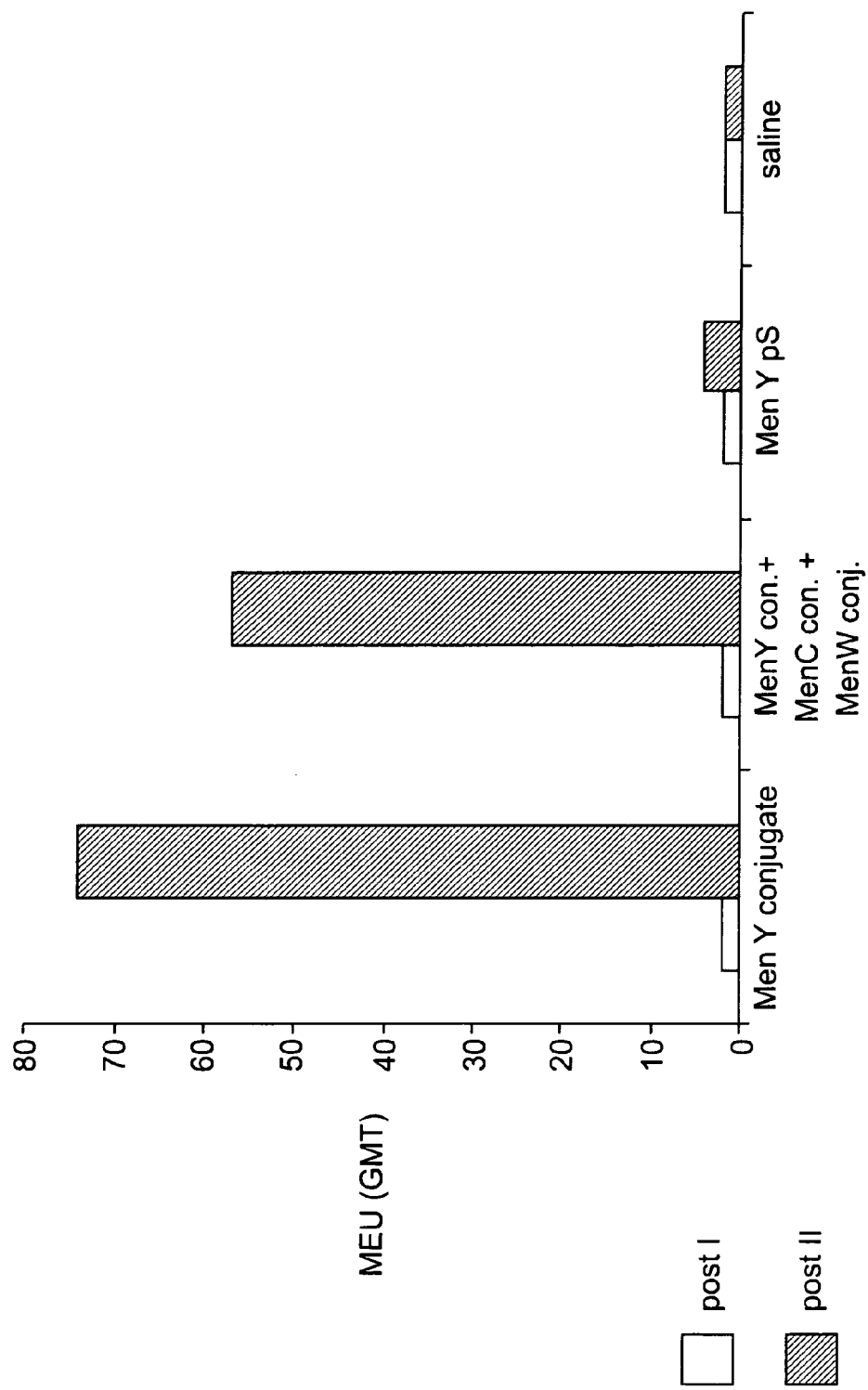
Figure 8:
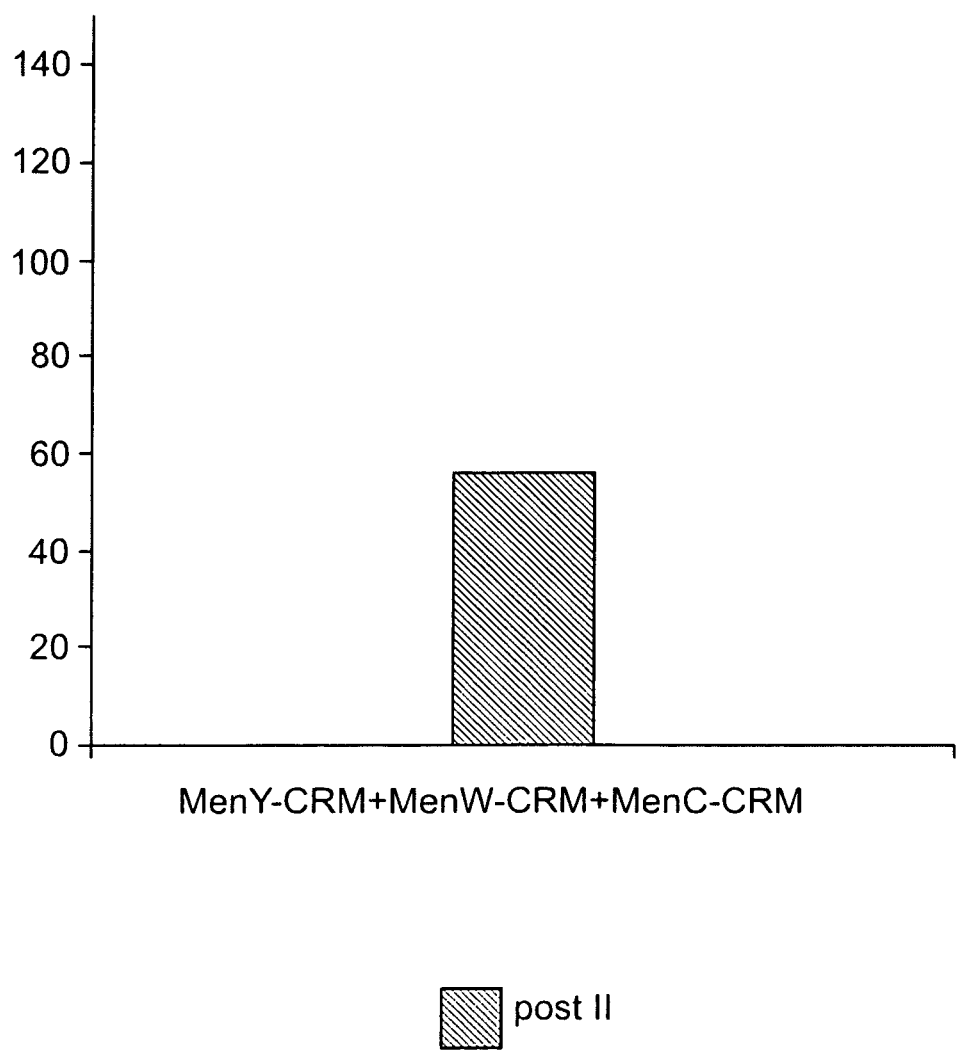

The results show that the immunogenicity of MenW135 conjugate is enhanced when administered in combination with MenC and MenY conjugates, when compared to that obtained with the MenW135 conjugate alone (FIG. 6). MenY immunogenicity was comparable in the combination to that obtained with the individual conjugate (FIG. 7) and was also comparable to the immunogenicity of the MenC conjugate (FIG. 8).

H. Combination Vaccine for Serogroups A, C, W135 and Y

Conjugates of polysaccharides from serogroups A, C, W135 and Y were mixed as described above to give a final concentration of 20 μg saccharide/ml for the serogroup A, W135 and Y conjugates and 5 μg saccharide/ml for the serogroup C conjugate. The vaccine contained a final concentration of 5 mM sodium phosphate, 9 mg/ml NaCl, aluminium phosphate (to give an $Al^{3+}$ concentration of 0.6 mg/ml), pH 7.2. The mixture was then kept, without stirring, at 2-8° C. overnight and further diluted with saline to give 4 μg saccharide/ml for the A, W135 and Y conjugates and 1 μg saccharide/ml for the C conjugate. This diluted mixture was used for immunisation.

Immunisations and analysis took place as before, with controls including the individual conjugates except for serogroup C.

Figure 9:
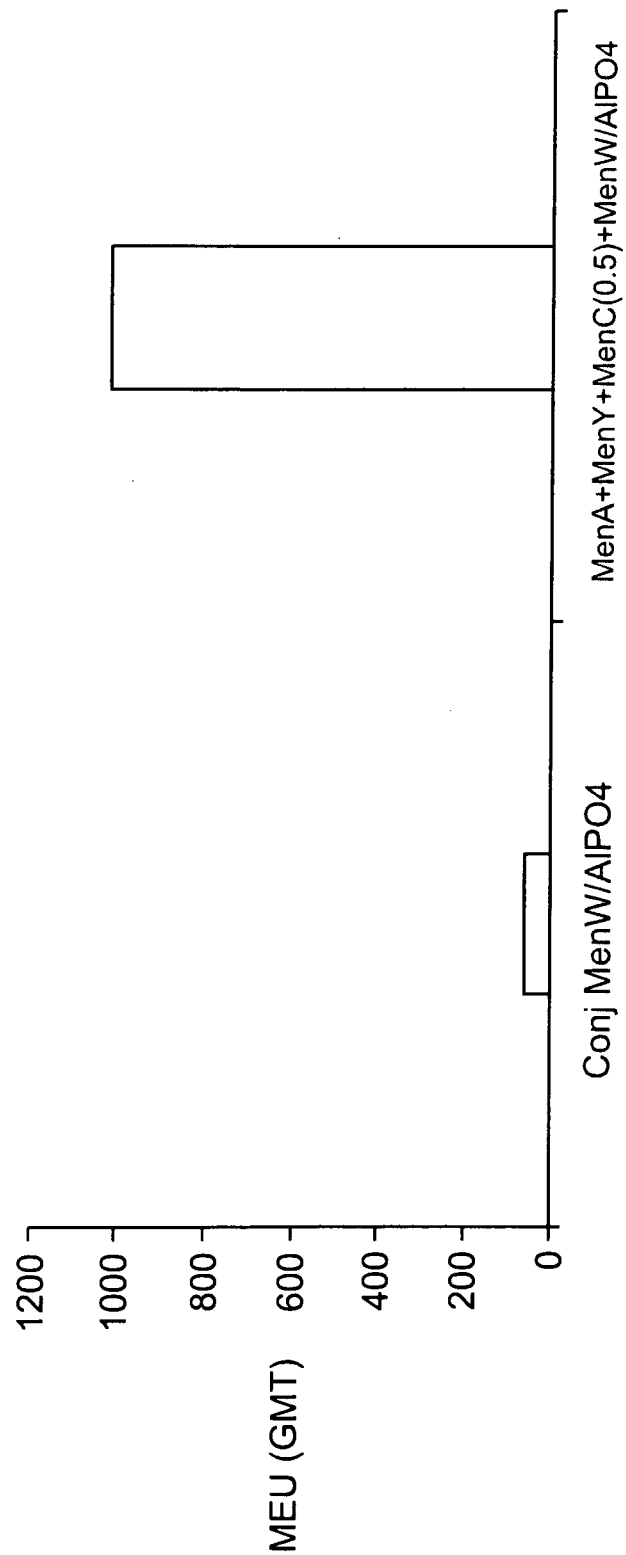
FIGS. 9 to 11 show post-II IgG titres obtained in mice with a mixture of oligosaccharide conjugates for serogroups A, C, W135 and Y.
Figure 10:
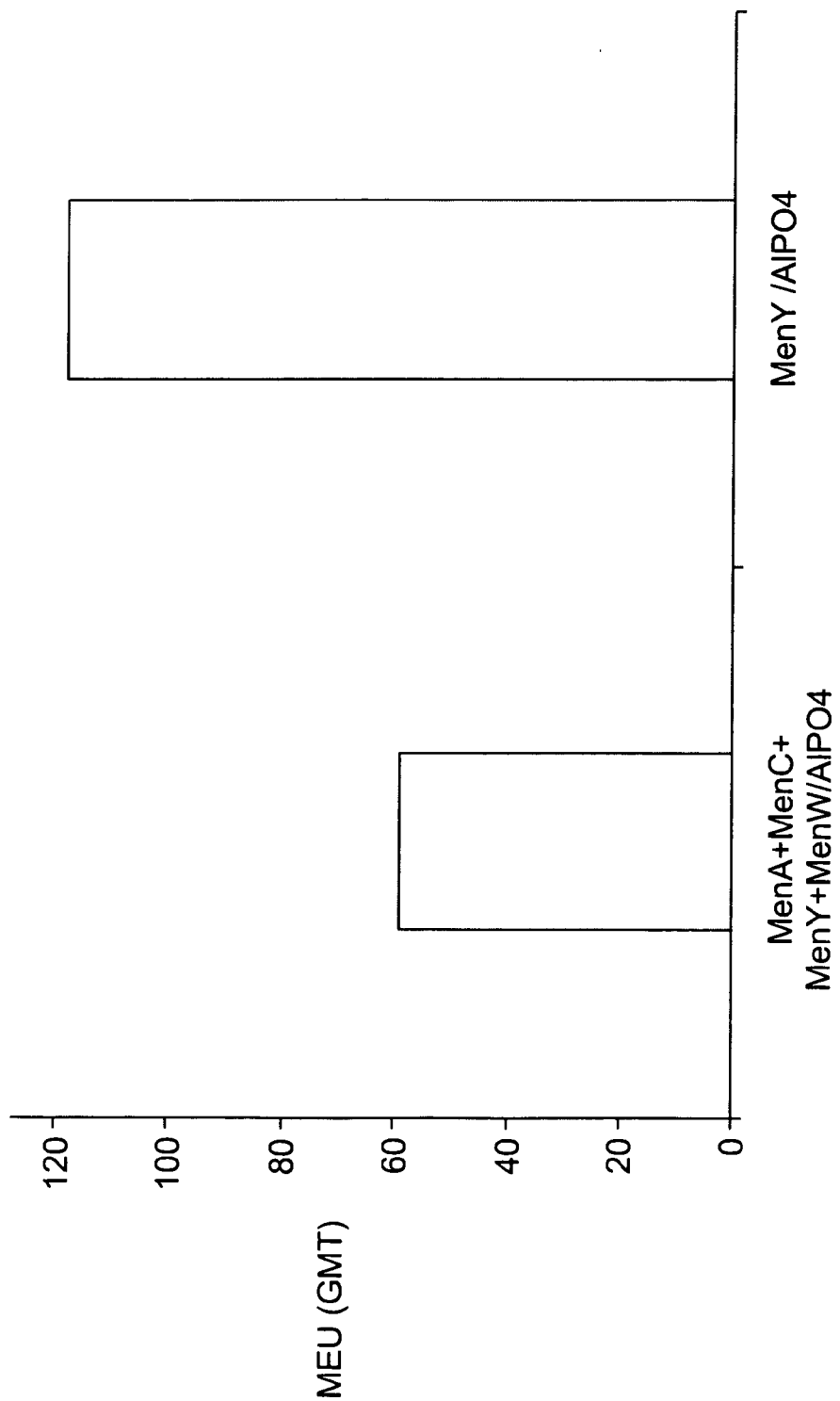
Figure 11:
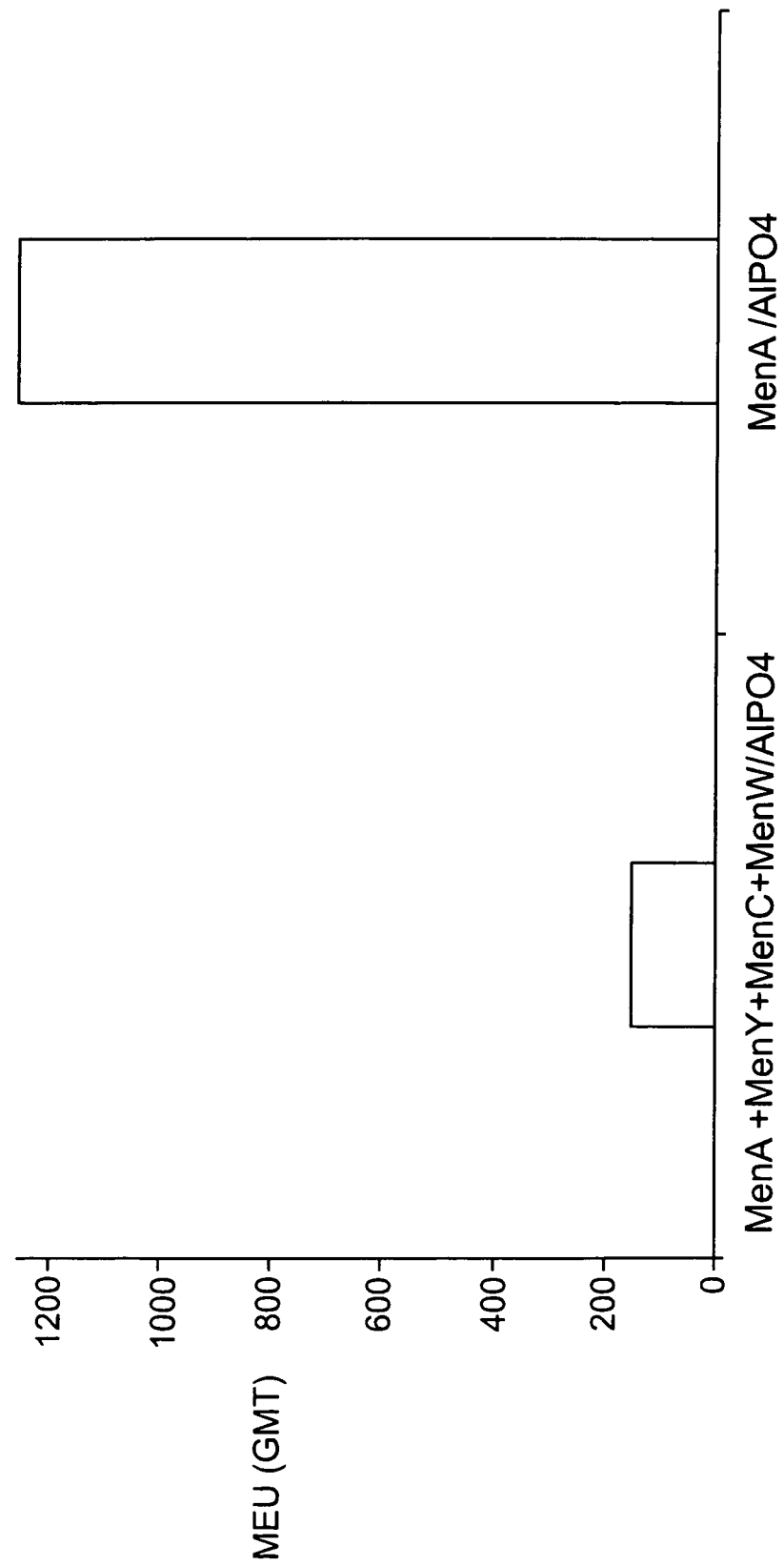

FIG. 9 shows that, as before, the immunogenicity of the MenW135 conjugate was enhanced when administered in combination with the MenA, MenC and MenY conjugates. FIG. 10 shows that the immunogenicity of the MenY conjugate is not significantly different when delivered in combination with the MenA, MenC and MenW135 conjugates. FIG. 11 shows that the immunogenicity of the MenA conjugate decreases markedly in the combination, even with the MenC conjugate administered at a lower dosage (¼).

This antigenic competition is not seen in the non-conjugated tetravalent (ACWY) polysaccharide vaccine [5].

I. Lyophilised Serogroup A Antigen

The capsular polysaccharide of serogroup A *N. meningitidis* is particularly susceptible to hydrolysis. Conjugates of MenA capsular oligosaccharide were therefore prepared in lyophilised form, ready for re-constitution at the time of administration. The lyophilised form was prepared to have components which give the following composition after reconstitution into a unit dose:

| Component | Concentration |
| --- | --- |
| CRM-MenA | 20 μg saccharide/ml |
| Potassium phosphate buffer | 5 mM |
| Mannitol | 15 mg/ml |

This composition has no adjuvant. Two adjuvants were prepared for its reconstitution:

| Component | Concentration | Concentration |
| --- | --- | --- |
| Aluminium hydroxide | 0.68 mg $Al^{3+}$/ml | — |
| Aluminium phosphate* | — | 0.6 mg $Al^{3+}$/ml |
| Sodium phosphate buffer | — | 10 mM |
| Histidine buffer | 10 mM | — |
| Sodium chloride | 9 mg/ml | 9 mg/ml |
| Tween 80 | 0.005% | 0.005% |
| PH | 7.2 ± 0.05 | 7.2 ± 0.05 |

*amorphous hydroxyphosphate, $PO_4$/Al molar ratio between 0.84 and 0.92

When reconstituted with water for injection, stability of the saccharide component was as follows:

| | Stored at 2-8° C. | | | Stored at 36-38° C. | | |
| --- | --- | --- | --- | --- | --- | --- |
| Time (days) | Total saccharide (μg/ml) | Free saccharide (μg/ml) | Free saccharide % | Total saccharide (μg/ml) | Free saccharide (μg/ml) | Free saccharide % |
| 0 | 17.72 | 1.04 | 5.9 | 17.72 | 1.04 | 5.9 |
| 15 | 17.01 | 0.88 | 5.2 | 16.52 | 2.26 | 13.7 |
| 30 | 17.82 | 0.89 | 5.0 | 17.29 | 2.64 | 15.3 |

Over the same 4 Week time scale, pH was stable at 7.2 both at 2-8° C. and at 36-38° C., protein content was stable at around 24.5 μg/ml, and moisture content was below 2.5%.

When reconstituted with the aluminium phosphate adjuvant solution at and stored at 2-8° C., stability was as follows:

| Time (hours) | Total saccharide (μg/ml) | Free saccharide (μg/ml) | Free saccharide % |
| --- | --- | --- | --- |
| 0 | 16.62 | 1.09 | 6.6 |
| 24 | 16.51 | 0.98 | 5.9 |
| 48 | 16.83 | 0.99 | 5.9 |

J. Combination Vaccine for Serogroups A, C, W135 and Y (Lyophilised Serogroup A Conjugate)

A trivalent mixture of the MenC, W135 and Y components either adsorbed onto an aluminium hydroxide adjuvant (2 mg/ml) or mixed with an aluminium phosphate adjuvant (amorphous hydroxyphosphate, $PO_4$/Al molar ratio between 0.84 and 0.92, 0.6 mg/ml $Al^{3+}$, in presence of 10 mM phosphate buffer) was prepared. The compositions of the two trivalent mixtures were as follows:

| Component | Concentration | Concentration |
|---|---|---|
| Aluminium hydroxide | 0.68 mg $Al^{3+}$/ml | — |
| Aluminium phosphate* | — | 0.6 mg $Al^{3+}$/ml |
| CRM-MenC | 20 μg saccharide/ml | 20 μg saccharide/ml |
| CRM-MenY | 20 μg saccharide/ml | 20 μg saccharide/ml |
| CRM-MenW135 | 20 μg saccharide/ml | 20 μg saccharide/ml |
| Sodium phosphate buffer | — | 10 mM |
| Histidine buffer | 10 mM | — |
| Sodium chloride | 9 mg/ml | 9 mg/ml |
| Tween 80 | 0.005% | 0.005% |

*amorphous hydroxyphosphate, $PO_4/Al$ molar ratio between 0.84 and 0.92

For the hydroxide mixture, stability of the saccharide components were as follows:

| | Stored at 2-8° C. | | Stored at 36-38° C. | |
|---|---|---|---|---|
| Time (days) | Free saccharide (μg/ml) | Free saccharide % | Free saccharide (μg/ml) | Free saccharide % |
| | MenC bulk | | | |
| 0 | <1.2 | <6 | <1.2 | <6 |
| 15 | <1.2 | <6 | <1.2 | <6 |
| 30 | <1.2 | <6 | <1.2 | <6 |
| | MenC vials | | | |
| 0 | <1.2 | <6 | <1.2 | <6 |
| 15 | <1.2 | <6 | <1.2 | <6 |
| 30 | <1.2 | <6 | 1.3 | 6.6 |
| | MenW135 bulk | | | |
| 0 | 2.5 | 12.5 | 2.5 | 12.5 |
| 15 | 2.3 | 11.4 | 3.4 | 16.8 |
| 30 | 2.3 | 11.5 | 3.5 | 17.3 |
| | MenW135 vials | | | |
| 0 | 2.1 | 10.6 | 2.1 | 10.6 |
| 15 | 2.3 | 11.7 | 2.7 | 13.3 |
| 30 | 20. | 10.2 | 3.3 | 16.3 |
| | MenY bulk | | | |
| 0 | 1.7 | 8.3 | 1.7 | 8.3 |
| 15 | <1.3 | <6.3 | 2.0 | 10.2 |
| 30 | 1.3 | 6.3 | 2.4 | 12.2 |
| | MenY vials | | | |
| 0 | 1.4 | 7.1 | 1.4 | 7.1 |
| 15 | 1.5 | 7.6 | 2.1 | 10.7 |
| 30 | 1.3 | 6.3 | 2.9 | 14.3 |

Over the same 4 week time scale, pH was stable at 7.15±0.05 both at 2-8° C. and at 36-38° C.

For the phosphate mixture, stability of the saccharide components were as follows:

| | Stored at 2-8° C. | | | Stored at 36-38° C. | | |
|---|---|---|---|---|---|---|
| Time (days) | Total saccharide (μg/ml) | Free saccharide (μg/ml) | Free saccharide % | Total saccharide (μg/ml) | Free saccharide (μg/ml) | Free saccharide % |
| | MenC bulk | | | | | |
| 0 | 22.8 | <1.0 | <5 | 22.8 | <1.0 | <5 |
| 15 | 17.2 | <1.0 | <5 | 18.6 | <1.0 | <5 |
| 30 | 18.9 | <1.0 | <5 | 20.5 | <1.0 | <5 |
| | MenC vials | | | | | |
| 0 | 20.5 | <1.0 | <5 | 20.5 | <1.0 | <5 |
| 15 | 18.3 | <1.0 | <5 | 23.4 | <1.0 | <5 |
| 30 | 18.0 | <1.0 | <5 | 20.5 | <1.0 | <5 |
| | MenW135 bulk | | | | | |
| 0 | 20.7 | 2.0 | 10.4 | 20.7 | 2.0 | 10.4 |
| 15 | 21.9 | 2.3 | 11.6 | 21.2 | 2.1 | 10.3 |
| 30 | 19.6 | 2.1 | 10.6 | 21.0 | 2.4 | 11.8 |
| | MenW135 vials | | | | | |
| 0 | 23.4 | 1.7 | 8.4 | 23.4 | 1.7 | 8.4 |
| 15 | 21.2 | 1.9 | 9.5 | 20.1 | 2.2 | 11.1 |
| 30 | 20.1 | 2.2 | 11.2 | 21.3 | 3.2 | 16.1 |
| | MenY bulk | | | | | |
| 0 | 19.1 | <1.1 | <5.3 | 19.1 | <1.1 | <5.3 |
| 15 | 20.1 | 1.4 | 6.8 | 18.7 | 1.3 | 6.4 |
| 30 | 18.6 | 1.4 | 7.6 | 19.2 | 1.7 | 8.3 |
| | MenY vials | | | | | |
| 0 | 21.4 | <1.1 | <5.3 | 21.4 | <1.1 | <5.3 |
| 15 | 19.6 | 1.4 | 6.8 | 19.0 | 1.5 | 7.4 |
| 30 | 17.7 | 1.2 | 6.2 | 18.4 | 1.9 | 9.4 |

Over the same 4 week time scale, pH was stable at 7.05±0.05 both at 2-8° C. and at 36-38° C.

The trivalent liquid compositions were diluted and 0.5 ml used to reconstitute the lyophilised MenA conjugate. The resulting tetravalent mixture was administered to ten Balb/c mice (female 6-8 weeks old) per group by subcutaneous injection at day 0 and 28. The mixture contained 2 µg of each saccharide conjugate per dose, which represents ⅕ of the single human dose (SHD). Controls were saline or unconjugated homologous polysaccharides. Bleedings were performed before immunization and then at day 42, with sera stored at −70° C. IgG was determined as described above.

All the conjugates used were safe and immunogenic in the animals. GMT post-II ELISA titres (with 95% confidence intervals) were as follows:

| Vaccine | Adjuvant | A | Y | W135 | C |
|---|---|---|---|---|---|
| MenA (lyophilised and resuspended) | Aluminium phosphate | 172 (69-439) | — | — | — |
| | Aluminium hydroxide | 619 (419-906) | — | — | — |
| MenY | Aluminium phosphate | — | 328 (147-731) | — | — |
| | Aluminium hydroxide | — | 452 (344-593) | — | — |
| MenW | Aluminium phosphate | — | — | 80 (28-225) | — |
| | Aluminium hydroxide | — | — | 277 (185-411) | — |
| MenC | Aluminium phosphate | — | — | — | 317 (152-659) |
| | Aluminium hydroxide | — | — | — | 723 (615-851) |
| MenA (lyophilized) + MenC, W135, Y | Aluminium phosphate | 32 (15-68) | 397 (252-627) | 99 (35-288) | 114 (53-246) |
| | Aluminium hydroxide | 206 (112-372) | 141 (97-205) | 139 (76-251) | 163 (122-218) |

FIG. 17 shows the results of IgG subclass analysis for: (17A) MenA; (17B) MenC; (17C) MenW135; and (17D) MenY. IgG1 is clearly the most prominent subclass.

Serum bactericidal titres were as follows:

| Vaccine | Adjuvant | Anti-MenA | | | Anti-MenY | | Anti-MenW135 | | Anti-MenC |
|---|---|---|---|---|---|---|---|---|---|
| | | F8238 | A1 | F6124 | 242975 | 240539 | 5554 | 242317 | C11 |
| MenA (lyophilised) | Aluminium phosphate | 512-1024 | 1024-2048 | 2048 | — | — | — | — | — |
| | Aluminium hydroxide | 1024-2048 | 1024-2048 | 2048 | — | — | — | — | — |
| MenY | Aluminium phosphate | — | — | — | 4096 | 2048-4096 | — | — | — |
| | Aluminium hydroxide | — | — | — | 2048 | 1024-2048 | — | — | — |
| MenW | Aluminium phosphate | — | — | — | — | — | 512 | 512-1024 | — |
| | Aluminium hydroxide | — | — | — | — | — | 1024 | 1024-2048 | — |
| MenC | Aluminium phosphate | — | — | — | — | — | — | — | 2048-4096 |
| | Aluminium hydroxide | — | — | — | — | — | — | — | 4096 |
| MenA (lyophilized) + MenC, W135, Y | Aluminium phosphate | 128-256 | 1024 | 1024-2048 | 2048 | — | 256-512 | 1024 | 512 |
| | Aluminium hydroxide | 512 | 1024-2048 | 1024-2048 | 2048-4096 | — | 256-512 | 1024 | 512-1024 |

K. Combination Vaccine for Serogroups A, C, W135 and Y (Different Dosages)

Mice were immunised as described above, but the vaccine compositions contained different ratios of the various oligosaccharide conjugates. Doses were variously 0.5, 1, 2 or 4 µg/dose. Lyophilised MenA oligo-conjugate was used in all experiments.

ELISA titres were as follows:

| Antigen quantity (µg/dose) | | | | Aluminium | GMT ELISA (95% confidence interval) | | | |
|---|---|---|---|---|---|---|---|---|
| A | C | W135 | Y | adjuvant | A | C | W135 | Y |
| 4 | 2 | 2 | 2 | Phosphate | 177 (107-291) | 367 (263-510) | 239 (135-424) | 239 (184-311) |
| 4 | 2 | 2 | 2 | Hydroxide | 390 (313-486) | 494 (345-706) | 338 (266-430) | 158 (96-260) |
| 2 | 2 | 2 | 2 | Phosphate | 132 (59-296) | 582 (268-1155) | 143 (75-272) | 247 (152-400) |
| 2 | 2 | 2 | 2 | Hydroxide | 337 (239-476) | 569 (462-679) | 171 (117-251) | 100 (59-169) |
| 4 | 2 | 1 | 1 | Phosphate | 137 (47-397) | 192 (88-421) | 18 (4-75) | 315 (174-571) |
| 4 | 2 | 1 | 0.5 | Phosphate | 152 (85-271) | 207 (100-428) | 51 (21-125) | 220 (125-388) |
| 4 | 2 | 1 | 2 | Phosphate | 113 (49-263) | 230 (98-540) | 23 (6-91) | 267 (81-877) |
| 4 | 2 | 0.5 | 1 | Phosphate | 267 (109-656) | 504 (300-847) | 46 (15-134) | 583 (330-1030) |
| 4 | 2 | 2 | 1 | Phosphate | 87 (49-155) | 118 (51-278) | 24 (8-72) | 214 (140-326) |
| 2 | 2 | 1 | 1 | Phosphate | 217 (132-355) | 514 (332-796) | 110 (66-183) | 206 (141-300) |
| 2 | 2 | 1 | 0.5 | Phosphate | 105 (40-279) | 381 (180-808) | 90 (34-236) | 206 (96-445) |
| 2 | 2 | 1 | 2 | Phosphate | 155 (71-339) | 374 (196-713) | 53 (28-100) | 502 (335-752) |
| 2 | 2 | 0.5 | 1 | Phosphate | 224 (125-400) | 358 (223-577) | 43 (14-128) | 624 (426-914) |
| 2 | 2 | 2 | 1 | Phosphate | 180 (113-288) | 306 (190-492) | 70 (34-146) | 423 (258-696) |

Serum bactericidal titres were as follows:

| Antigen quantity (µg/dose) | | | | Aluminium | Bactericidal antibody titre | | | |
|---|---|---|---|---|---|---|---|---|
| A | C | W135 | Y | adjuvant | A | C | W135 | Y |
| 4 | 2 | 2 | 2 | Phosphate | 256-512 | 1024-2048 | 1024-2048 | 4096-8192 |
| 4 | 2 | 2 | 2 | Hydroxide | 1024-2048 | 256-512 | 1024-2048 | 1024-2048 |
| 2 | 2 | 2 | 2 | Phosphate | 512-1024 | 1024-2048 | 128-256 | 8192-16384 |
| 2 | 2 | 2 | 2 | Hydroxide | 256 | 1024-2048 | 256 | 512-1024 |
| 4 | 2 | 1 | 1 | Phosphate | 512-1024 | 2048 | 128 | 2048-4096 |
| 4 | 2 | 1 | 0.5 | Phosphate | 512-1024 | 1024-2048 | 128 | 2048-4096 |
| 4 | 2 | 1 | 2 | Phosphate | 512-1024 | 2048-4096 | 128 | 8192-16384 |
| 4 | 2 | 0.5 | 1 | Phosphate | 1024-2048 | 8192 | 256-512 | 8192-16384 |
| 4 | 2 | 2 | 1 | Phosphate | — | 2048-4096 | 128 | 4096-8192 |
| 2 | 2 | 1 | 1 | Phosphate | 1024-2048 | 1024-2048 | 256 | 4096-8192 |
| 2 | 2 | 1 | 0.5 | Phosphate | 1024-2048 | 2048-4096 | 256-512 | 2048-4096 |
| 2 | 2 | 1 | 2 | Phosphate | 512-1024 | 1024-2048 | 128 | 8192-16384 |
| 2 | 2 | 0.5 | 1 | Phosphate | 1024-2048 | 2048 | 256-512 | 4096-8192 |
| 2 | 2 | 2 | 1 | Phosphate | 128-256 | 512-1024 | 64-128 | 1024-2048 |

A second set of experiments was performed using a dosage of 2 µg/ml saccharide for MenA and MenC, half that dosage for MenY, and a quarter dosage for MenW135. ELISA titres were as follows:

| Antigen quantity (µg/dose) | | | | Aluminium | GMT ELISA (95% confidence interval) | | | |
|---|---|---|---|---|---|---|---|---|
| A | C | W135 | Y | adjuvant | A | C | W135 | Y |
| 2 | 2 | 2 | 2 | Phosphate | 32 (15-68) | 114 (53-246) | 99 (35-288) | 397 (252-627) |
| | | | | Hydroxide | 206 (112-372) | 163 (122-218) | 139 (76-251) | 141 (97-205) |

-continued

| Antigen quantity (μg/dose) | | | | Aluminium adjuvant | GMT ELISA (95% confidence interval) | | | |
|---|---|---|---|---|---|---|---|---|
| A | C | W135 | Y | | A | C | W135 | Y |
| 2 | 2 | 0.5 | 1 | Phosphate | 96 (49-187) | 238 (101-561) | 42 (20-89) | 315 (114-867) |
| | | | | Hydroxide | 293 (144-597) | 267 (158-451) | 83 (43-163) | 244 (152-392) |

Serum bactericidal titres were as follows:

| Antigen quantity (μg/dose) | | | | Aluminium adjuvant | A | | | C | W135 | | Y |
|---|---|---|---|---|---|---|---|---|---|---|---|
| A | C | W | Y | | F8238 | A1 | F6124 | C11 | 5554 | 242317 | 242975 |
| 2 | 2 | 2 | 2 | Phosphate | 128-256 | 1024 | 1024-2048 | 512 | 256-512 | 1024 | 2048 |
| | | | | Hydroxide | 512 | 1024-2048 | 1024-2048 | 512-1024 | 256-512 | 1024 | 2048-4096 |
| 2 | 2 | 0.5 | 1 | Phosphate | 256 | — | 1024-2048 | 512 | 256-512 | 1024 | 2048-4096 |
| | | | | Hydroxide | 128 | — | 512-1024 | 512-1024 | 512-1024 | 1024 | 1024 |

L. MenA, W135 and Y Oligosaccharide Conjugates

The following table shows data relating to MenA, MenW135 and MenY conjugates suitable for making combination compositions of the invention:

| | A | W135 | Y |
|---|---|---|---|
| DP after sizing | 16.6 | 21.9 | 21.1 |
| Saccharide/protein ratio | 0.5 | 1.1 | 0.7 |
| KD | 0.44 | 0.36 | 0.41 |
| Free saccharide | 5% | 10% | 5% |
| Free protein | <2% | <2% | <2% |

It will be understood that the invention has been described by way of example only and modifications may be made whilst remaining within the scope and spirit of the invention.

REFERENCES

The Contents of which are Hereby Incorporated in Full

[1] Frash (1990) pp. 123-145 of *Advances in Biotechnological Processes* vol. 13 (eds. Mizrahi & Van Wezel)
[2] Armand et al. (1982) *J. Biol. Stand.* 10:335-339.
[3] Cadoz et al. (1985) *Vaccine* 3:340-342.
[4] MMWR (1997) 46(RR-5) 1-10.
[5] Baklaic et al. (1983) *Infect. Immun.* 42:599-604.
[6] Costantino et al. (1992) *Vaccine* 10:691-698.
[7] WO02/00249.
[8] Inzana (1987) *Infect. Immun.* 55:1573-1579.
[9] WO98/32873.
[10] U.S. Pat. No. 4,753,796.
[11] European patent 0072513.
[12] UK patent application 0207117.3.
[13] Pon et al. (1997) *J Exp Med* 185:1929-1938.
[14] Ravenscroft et al. (1999) *Vaccine* 17:2802-2816.
[15] Ramsay et al. (2001) *Lancet* 357(9251): 195-196.
[16] Lindberg (1999) *Vaccine* 17 Suppl 2:S28-36.
[17] Buttery & Moxon (2000) *J R Coll Physicians Lond* 34:163-168.
[18] Ahmad & Chapnick (1999) *Infect Dis Clin North Am* 13:113-133, vii.
[19] Goldblatt (1998) *J. Med. Microbiol.* 47:563-567.
[20] European patent 0477508.
[21] U.S. Pat. No. 5,306,492.
[22] WO98/42721.
[23] Dick et al. in *Conjugate Vaccines* (eds. Cruse et al.) Karger, Basel, 1989, Vol. 10, pp. 48-114.
[24] Hermanson *Bioconjugate Techniques*, Academic Press, San Diego (1996) ISBN: 0123423368.
[25] Anonymous (January 2002) *Research Disclosure*, 453077.
[26] Anderson (1983) *Infect Immun* 39(1):233-238.
[27] Anderson et al. (1985) *J Clin Invest* 76(1):52-59.
[28] EP-A-0372501.
[29] EP-A-0378881.
[30] EP-A-0427347.
[31] WO93/17712
[32] WO94/03208.
[33] WO98/58668.
[34] EP-A-0471177.
[35] WO91/01146
[36] Falugi et al. (2001) *Eur J Immunol* 31:3816-3824.
[37] WO00/56360.
[38] WO00/61761.
[39] WO99/42130
[40] WO96/40242
[41] Lees et al. (1996) *Vaccine* 14: 190-198.
[42] WO95/08348.
[43] U.S. Pat. No. 4,882,317
[44] U.S. Pat. No. 4,695,624
[45] *Mol. Immunol.*, 1985, 22, 907-919
[46] EP-A-0208375
[47] WO00/10599
[48] Gever et al., Med. Microbiol. Immunol, 165: 171-288 (1979).
[49] U.S. Pat. No. 4,057,685.
[50] U.S. Pat. Nos. 4,673,574; 4,761,283; 4,808,700.
[51] U.S. Pat. No. 4,459,286.
[52] U.S. Pat. No. 4,965,338
[53] U.S. Pat. No. 4,663,160.
[54] U.S. Pat. No. 4,761,283
[55] U.S. Pat. No. 4,356,170

[56] Lei et al. (2000) *Dev Biol (Basel)* 103:259-264.
[57] WO00/38711; U.S. Pat. No. 6,146,902.
[58] McLeod Griffiss et al. (1981) *Infect. Immun.* 34:725-732.
[59] WO99/24578.
[60] WO99/36544.
[61] WO99/57280.
[62] WO00/22430.
[63] Tettelin et al. (2000) *Science* 287:1809-1815.
[64] Pizza et al. (2000) *Science* 287:1816-1820.
[65] WO01/52885.
[66] Bjune et al. (1991) *Lancet* 338(8775):1093-1096.
[67] Fukasawa et al. (1999) *Vaccine* 17:2951-2958.
[68] Rosenqvist et al. (1998) *Dev. Biol. Stand.* 92:323-333.
[69] WO96/14086.
[70] Covacci & Rappuoli (2000) *J. Exp. Med.* 19:587-592.
[71] WO93/18150.
[72] Covacci et al. (1993) *Proc. Natl. Acad. Sci. USA* 90: 5791-5795.
[73] Tummuru et al. (1994) *Infect. Immun.* 61:1799-1809.
[74] Marchetti et al. (1998) *Vaccine* 16:33-37.
[75] Telford et al. (1994) *J. Exp. Med.* 179:1653-1658.
[76] Evans et al. (1995) *Gene* 153:123-127.
[77] WO96/01272 & WO96/01273, especially SEQ ID NO:6.
[78] WO97/25429.
[79] WO98/04702.
[80] Watson (2000) *Pediatr Infect Dis J* 19:331-332.
[81] Rubin (2000) *Pediatr Clin North Am* 47:269-285, v.
[82] Jedrzejas (2001) *Microbiol Mol Biol Rev* 65:187-207.
[83] Bell (2000) *Pediatr Infect Dis J* 19:1187-1188.
[84] Iwarson (1995) *APMIS* 103:321-326.
[85] Gerlich et al. (1990) *Vaccine* 8 Suppl:S63-68 & 79-80.
[86] WO93/24148.
[87] Costantino et al. (1999) *Vaccine* 17:1251-1263.
[88] WO97/00697.
[89] Hsu et al. (1999) *Clin Liver Dis* 3:901-915.
[90] WO02/02606.
[91] Kalman et al. (1999) *Nature Genetics* 21:385-389.
[92] Read et al. (2000) *Nucleic Acids Res* 28:1397-406.
[93] Shirai et al. (2000) *J. Infect. Dis.* 181 (Suppl 3):S524-S527.
[94] WO99/27105.
[95] WO00/27994.
[96] WO00/37494.
[97] WO99/28475.
[98] Ross et al. (2001) *Vaccine* 19:4135-4142.
[99] Sutter et al. (2000) *Pediatr Clin North Am* 47:287-308.
[100] Zimmerman & Spann (1999) *Am Fam Physician* 59:113-118, 125-126.
[101] Dreesen (1997) *Vaccine* 15 Suppl:S2-6.
[102] *MMWR Morb Mortal Wkly Rep* 1998 Jan. 16; 47(1): 12, 19.
[103] *Vaccines* (1988) eds. Plotkin & Mortimer. ISBN 0-7216-1946-0.
[104] McMichael (2000) *Vaccine* 19 Suppl 1:S101-107.
[105] Schuchat (1999) *Lancet* 353(9146):51-6.
[106] WO02/34771.
[107] Dale (1999) *Infect Dis Clin North Am* 13:227-43, viii.
[108] Ferretti et al. (2001) *PNAS USA* 98: 4658-4663.
[109] Kuroda et al. (2001) *Lancet* 357(9264): 1225-1240; see also pages 1218-1219.
[110] Anderson (2000) *Vaccine* 19 Suppl 1:S59-65.
[111] Kahn (2000) *Curr Opin Pediatr* 12:257-262.
[112] Crowe (1995) *Vaccine* 13:415-421.
[113] *J Toxicol Clin Toxicol* (2001) 39:85-100.
[114] Demicheli et al. (1998) *Vaccine* 16:880-884.
[115] Stepanov et al. (1996) *J Biotechnol* 44:155-160.
[116] Wassilak & Orenstein, Chapter 4 of *Vaccines* (eds. Plotkin & Mortimer), 1988.
[117] Gustafsson et al. (1996) *N. Engl. J. Med.* 334:349-355.
[118] Rappuoli et al. (1991) *TIBTECH* 9:232-238.
[119] WO97/28273.
[120] Lieberman et al. (1996) *JAMA* 275:1499-1503.
[121] WO00/56365.
[122] Gennaro (2000) *Remington: The Science and Practice of Pharmacy*. 20th ed ISBN: 0683306472
[123] *Vaccine Design* . . . (1995) eds. Powell & Newman. ISBN: 030644867X. Plenum.
[124] WO90/14837.
[125] U.S. Pat. No. 6,299,884.
[126] WO00/07621.
[127] WO99/44636.
[128] GB-2220221.
[129] EP-A-0689454.
[130] WO00/56358.
[131] EP-A-0835318.
[132] EP-A-0735898.
[133] EP-A-0761231.
[134] WO99/52549.
[135] WO01/21207.
[136] WO01/21152.
[137] WO00/62800.
[138] WO00/23105.
[139] WO99/11241.
[140] WO98/57659.
[141] Del Giudice et al. (1998) *Molecular Aspects of Medicine*, vol. 19, number 1.
[142] WO99/27960.
[143] WO98/20734.
[144] UK patent application 0118249.2.
[145] WO01/30390.
[146] Chen et al. (1956) *Anal. Chem.* (1956) 28:1756-1758.
[147] Habeeb et al. (1966) *Anal. Biochem.* 14:328-336.
[148] Miron & Wilchek (1982) *Anal. Biochem.* 126:433-435.
[149] Svennerholm (1957) *Biochem. Biophys. Acta* 24:604-611.
[150] Carlone et al (1992) *J. Clin. Microbiol.* 30:154-159.

The invention claimed is:

1. A process for conjugating a bacterial capsular saccharide to a carrier protein, comprising:
purifying the saccharide, comprising the steps of (a) precipitation of the saccharide using one or more cationic detergents, followed by (b) solubilisation of the precipitated saccharide using ethanol at a final concentration of between 75% and 95%,
conjugating the saccharide to a carrier protein, wherein the carrier protein is a bacterial toxin or toxoid, and wherein the conjugated saccharide has a saccharide: protein ratio (w/w) between 0.5:1 and 5:1,
mixing the conjugated saccharide with a second bacterial capsular saccharide conjugated to a second carrier protein, wherein the second carrier protein is the bacterial toxin or toxoid,
wherein the bacterial capsular saccharide is from *Neisseria meningitidis* serogroup A, W135 or Y, or from *Haemophilus influenzae*, or from *Streptococcus pneumoniae*.

2. A process for conjugating a bacterial capsular saccharide to a carrier protein, comprising:
purifying the saccharide, comprising the steps of (a) precipitation of the saccharide using one or more cationic detergents, followed by (b) solubilisation of the precipitated saccharide using ethanol at a final concentration of between 75% and 95%, activating the saccharide with a cyanylating reagent, and conjugating the saccharide to a carrier protein, wherein the carrier protein is a bacterial toxin or toxoid, mixing the conjugated saccharide with a second bacterial capsular saccharide conjugated to a second carrier protein, wherein the second carrier protein is the bacterial toxin or toxoid, wherein the bacterial capsular saccharide is from *Neisseria meningitidis* serogroup A, W135 or Y, or from *Haemophilus influenzae*, or from *Streptococcus pneumoniae*.

3. The process of claim 1 or claim 2, wherein the cationic detergent(s) comprise a cetyltrimethylammonium salt, a tetrabutylammonium salt, a myristyltrimethylammonium salt and/or hexadimethrine bromide.

4. The process of claim 1 or claim 2, wherein the saccharide obtained in step (b) is then precipitated.

5. The process of claim 4, wherein precipitation is by addition of calcium or sodium salts.

6. The process of claim 1 or claim 2, wherein the carrier protein is diphtheria toxoid or tetanus toxoid.

7. The process of claim 1 or claim 2, wherein, after conjugation, free and conjugated saccharides are separated.

8. The process of claim 7, wherein separation uses hydrophobic chromatography, tangential ultrafiltration, or diafiltration.

9. The process of claim 1 or claim 2, wherein the step of mixing the conjugated saccharide with the second bacterial capsular saccharide conjugated to a second carrier protein gives a mixture of saccharides from more than one serogroup of *N. meningitidis*.

10. The process of claim 9, wherein saccharide antigens from *N. meningitidis* strains A, C, W135 and/or Y are mixed.

11. The process of claim 10, wherein mixing gives a composition comprising capsular saccharides from both serogroups A and C and the ratio (w/w) of MenA saccharide: MenC saccharide is 2:1.

12. The process of claim 10, wherein mixing gives a composition comprising capsular saccharides from serogroup Y and one or both of serogroups C and W135, and wherein the ratio (w/w) of MenY saccharide:MenW135 saccharide is greater than 1 and/or that the ratio (w/w) of MenY saccharide:MenC saccharide is less than 1.

13. The process of claim 10, wherein mixing gives a composition comprising capsular saccharides from serogroups A, C, W135 and Y, and wherein serogroups A:C: W135:Y have ratios (w/w) of 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; or 2:2:2:1.

14. The process of claim 1 or claim 2, further comprising step(s) of vaccine formulation comprising mixing the saccharide antigen(s) with an adjuvant which is an aluminium phosphate and/or an aluminium hydroxide.

* * * * *